United States Patent
Axelrod et al.

(10) Patent No.: US 10,512,414 B2
(45) Date of Patent: Dec. 24, 2019

(54) APPARATUS AND METHOD FOR DETECTING GASTROINTESTINAL MOTOR ACTIVITY DURING POST-OPERATIVE RECOVERY

(71) Applicant: G-Tech Medical, Inc., Mountain View, CA (US)

(72) Inventors: Steve Axelrod, Los Altos, CA (US); Anand Navalgund, San Jose, CA (US)

(73) Assignee: G-Tech Medical, Inc., Mountain View, CA (US)

( * ) Notice: Subject to any disclaimer, the term of this patent is extended or adjusted under 35 U.S.C. 154(b) by 194 days.

(21) Appl. No.: 15/249,695

(22) Filed: Aug. 29, 2016

(65) Prior Publication Data
US 2017/0055871 A1 Mar. 2, 2017

Related U.S. Application Data

(60) Provisional application No. 62/211,747, filed on Aug. 29, 2015.

(51) Int. Cl.
*A61B 5/0488* (2006.01)
*A61B 5/0492* (2006.01)
(Continued)

(52) U.S. Cl.
CPC ........ *A61B 5/04884* (2013.01); *A61B 5/0492* (2013.01); *A61B 5/7203* (2013.01);
(Continued)

(58) Field of Classification Search
CPC . A61B 5/04884; A61B 5/0492; A61B 5/7203; A61B 5/04014; A61B 5/4255;
(Continued)

(56) References Cited

U.S. PATENT DOCUMENTS

| | | | |
|---|---|---|---|
| 5,704,368 A | 1/1998 | Asano et al. | |
| 5,795,304 A * | 8/1998 | Sun | A61B 5/04884 600/546 |

(Continued)

FOREIGN PATENT DOCUMENTS

| | | |
|---|---|---|
| WO | 199610358 A1 | 4/1996 |
| WO | 2010068818 A2 | 6/2010 |

(Continued)

OTHER PUBLICATIONS

Wienbeck, M., & Altaparmakov, I. (1981). Simultaneous electromyographic and manometric study of the function of the anorectum. Zeitschrift Fur Gastroenterologie, 19(7), 329-337. Retrieved from https://dialog.proquest.com/professional/docview/695139397?accountid=142257.*

(Continued)

*Primary Examiner* — Daniel L Cerioni
*Assistant Examiner* — Raymond P Dulman
(74) *Attorney, Agent, or Firm* — Aurora Consulting LLC; Ashley Sloat

(57) ABSTRACT

System and methods for acquiring and processing myoelectrical data from the gastrointestinal tract of a patient are provided. In various embodiments, the systems and methods monitor the motor activity of a patient recovering from surgery to detect a resumption in gastrointestinal motility. In some embodiments, the systems and methods enable proper post-operative ileus in the patient. In some embodiments, the systems and methods allow researchers or clinicians to determine the efficacy of one or more therapies intended to encourage gastrointestinal motility. In some embodiments, the systems and methods enable clinicians to predict and facilitate the proper timing of discharge from a healthcare facility following surgery.

21 Claims, 9 Drawing Sheets

(51) Int. Cl.
*A61B 5/00* (2006.01)
*A61B 5/04* (2006.01)

(52) U.S. Cl.
CPC ........ *A61B 5/7257* (2013.01); *A61B 5/04014* (2013.01); *A61B 5/4238* (2013.01); *A61B 5/4255* (2013.01); *A61B 5/6833* (2013.01); *A61B 2562/04* (2013.01)

(58) Field of Classification Search
CPC ... A61B 5/4238; A61B 5/7246; A61B 5/7264; A61B 5/7275; A61B 5/7282
See application file for complete search history.

(56) References Cited

U.S. PATENT DOCUMENTS

| | | | |
|---|---|---|---|
| 5,857,980 A * | 1/1999 | Wilson | A61B 5/04884 600/546 |
| 6,351,665 B1 * | 2/2002 | Koch | A61B 5/04884 600/546 |
| 7,160,254 B2 | 1/2007 | Noar | |
| 7,593,768 B1 | 9/2009 | Vasilev et al. | |
| 9,955,914 B2 * | 5/2018 | Dunki-Jacobs | A61B 5/4839 |
| 2003/0069714 A1 | 4/2003 | Wigley et al. | |
| 2004/0260164 A1 | 12/2004 | Kilcoyne et al. | |
| 2005/0209709 A1 | 9/2005 | Bradshaw | |
| 2005/0215917 A1 | 9/2005 | Noar | |
| 2006/0058606 A1 | 3/2006 | Davis et al. | |
| 2006/0107954 A1 | 5/2006 | Katz et al. | |
| 2006/0149541 A1 | 7/2006 | Jaklitsch et al. | |
| 2006/0258927 A1 | 11/2006 | Edgar, Jr. et al. | |
| 2007/0150007 A1 | 6/2007 | Anderson et al. | |
| 2007/0225576 A1 | 9/2007 | Brown et al. | |
| 2007/0287931 A1 | 12/2007 | Dilorenz | |
| 2008/0154110 A1 | 6/2008 | Burnes et al. | |
| 2009/0318783 A1 | 12/2009 | Rohde et al. | |
| 2010/0172839 A1 | 7/2010 | Walker | |
| 2010/0228105 A1 | 9/2010 | Policker et al. | |
| 2010/0292606 A1 | 11/2010 | Prakash et al. | |
| 2013/0046150 A1 | 2/2013 | Devanaboyina | |
| 2014/0226158 A1 | 8/2014 | Trainer | |
| 2014/0275886 A1 * | 9/2014 | Teixeira | A61B 5/0205 600/324 |
| 2016/0103967 A1 * | 4/2016 | Bulut | G16H 40/63 705/2 |
| 2016/0121111 A1 * | 5/2016 | Levine | A61N 1/36007 607/40 |
| 2016/0296157 A1 * | 10/2016 | Girouard | A61B 5/4094 |

FOREIGN PATENT DOCUMENTS

| | | |
|---|---|---|
| WO | 2010121038 A1 | 10/2010 |
| WO | 2012060874 A2 | 5/2012 |

OTHER PUBLICATIONS

Madsen, et al., Listening to Bowel Sounds: An Evidence-Based Practice Project, Dec. 2005, AJN, vol. 105, No. 12, p. 40-48.*
Haddab, S. et al., "Microcontroller-Based System for Electrogastrography Monitoring Through Wireless Transmission," Measurement Science Review, 2009,p. 122-126, vol. 9, No. 5.
Chen, J. D. Z. et al., "Detection of gastric slow wave propagation from the cutaneous electrogastrogram," Am J Physiol, 1999, p. G424-G430 vol. 277.
Kim, D. W. et al., "Usefulness of a Developed Four-Channel EGG System with running spectrum analysis," Yonsei Medical Journal, 2000, p. 230-236, vol. 41. No. 2.
Garcia-Casado, J. et al., "Noninvasive Measurement and Analysis of Intestinal Myoelectrical Activity Using Surface Electrodes," IEEE Transactions on Biomedical Engineering, Jun. 2005, p. 983-991, vol. 52, No. 6.
Chen, J. D. Z. et al., "Measurement of Electrical Activity of the Human Small Intestine Using Surface Electrodes," IEEE Transactions on Biomedical Engineering, Jun. 1993, p. 598-602, vol. 40, No. 6.
Lammers, W. J. E. P et al., "Orgin and propagation of the slow wave in the canine stomach: the outlines of a gastric conduction system," Am J Physiol Gastrointest Liver Physiol, 2009, p. G1200-G1210, vol. 296.
Leahy, A. et al., "Abnormalities of the Electrogastrogram in Functional Gastrointestinal Disorders," American Journal of Gastroenterology, 1999, p. 1023-1028, vol. 94, No. 4.
Myers, T. J. et al., "Human Surface Electrogastrograms: AC and DC measurements," Annals of Biomedical Engineering, 1984, p. 319-333, vol. 12.
Wang, Z. S. et al., "Detection of gastric slow wave uncoupling from multi-channel electrogastrogram: validations and applications," Neurogastroenterol Motil, 2003, p. 457-465, vol. 15.
Written Opinion issued on PCT Application Serial No. PCT/US2011/01848 by ISA/US dated May 21, 2012, p. 1-5.
International Search Report issued on PCT Application Serial No. PCT/US2011/01848 by ISA/US dated May 21, 2012, p. 1-4.
International Search Report and Written Opinion issued for PCT/US2015/056282 by ISA/US dated Jan. 20, 2016, 9 pages.
"Home—ePatch," DELTA Danish Electronics, Light & Acoustics, [Accessed Jul. 1, 2016] <http://epatch.madebydelta.com>.
Haahr, R. et al., "A wearable 'electronic patch' for wireless continuous monitoring of chronically diseased patients," 5th International Summer School and Symposium on Medical Devices and Biosensors, 2008, p. 66-70.
Sanders, K. M. et al., "Interstitial cells of Cajal as pacemakers in the gastrointestinal tract," Annu Rev Physiol, 2006, p. 307-343, vol. 68.

* cited by examiner

APPARATUS AND METHOD FOR DETECTING GASTROINTESTINAL MOTOR ACTIVITY DURING POST-OPERATIVE RECOVERY

CROSS-REFERENCE TO RELATED APPLICATIONS

This application claims priority to U.S. provisional patent Ser. No. 62/211,747, filed Aug. 29, 2015, which is herein incorporated by reference in its entirety.

TECHNICAL FIELD

This disclosure relates generally to systems and methods for profiling electrical activity within the smooth muscle of the gastrointestinal tract, and more particularly, to systems and methods for processing electronic recordings arising from electromyographic activity of the gastrointestinal tract in order to evaluate the degree of motor activity of the major gastrointestinal organs following surgical interventions known to cause temporary or extended ileus.

BACKGROUND

Patients undergoing abdominal or thoracic surgery remain hospitalized during recovery following such procedures. Even after patients are mobile and the risks of infection are minimal, patients are not discharged until they have demonstrated normal bowel function, most often via passage of gas and/or a bowel movement. Depending on the specific surgery, the typical length of stay (LOS) in the hospital is three or four days post-surgery. There is also a risk that the patient will not demonstrate normal bowel function in the typical timeframe and will need to remain in the hospital for several additional days or more. The likelihood of such an outcome varies by type of surgery and ranges from a few percent to upwards of twenty percent. When this situation arises, the patient is said to have developed post-operative ileus (POI).

Owing to the resulting distress to the patient of an extended LOS, risks of secondary infection, and cost to the healthcare system, it is an aim of most healthcare systems to avoid such cases of POI. It is a further aim to accelerate the discharge of patients not developing POI in order to minimize the hospital stay while also ensuring patient readiness for discharge and minimizing the likelihood of hospital readmission.

Motor activity, the muscular action of the smooth muscles in the walls of the stomach, small intestine, and colon under control of the enteric nervous system, mixes and propels the contents of these organs (i.e., chyme). This action supports digestion and drives motility, the normal movement of the thyme through the body, including eventual defecation. Immediately following abdominal and similar surgery, motor activity halts, gradually recovering over the next few days, organ by organ. Current literature estimates that during the post-operative period, the motor activity of the small intestine recovers within 8 to 24 hours, of the stomach at about 24 hours, and of the colon between 36 to 48 hours, while noting that these estimates contain considerable uncertainty due to a lack of direct measurements.

Unfortunately, at present, no reliable means of assessing the recovery of the GI tract exist short of the endpoint determination of flatus and bowel movement. Hospital staff and physicians monitor a patient's willingness to consume liquids and liquid meals, check for signs of nausea afterward, and periodically listen for abdominal sounds with a stethoscope during the first days after surgery. Yet none of these are reliable signs of incipient recovery of normal GI tract function. All have known weaknesses delineated in the literature.

U.S. Pat. No. 5,301,679 by Taylor teaches a means of measuring bowel sounds and relating the recordings to bowel activity, with an aim of addressing the same issue discussed here. This represents an automated version of the stethoscope technique, and underscores the need for a means of determining motor activity of the GI tract during surgical recovery. The approach suffers from the same fundamental limitation of the stethoscope in that the relationship of sounds recorded at the abdominal surface to motor activity is not well established. In fact, this approach is viewed by many as an unreliable indicator of motor activity.

Accordingly, there is a need for systems and methods that are able to directly measure the motor activity of the stomach, small intestine, and colon as they recover function, to monitor the recovery of said organs after surgery. With this information, hospital staff would be able to determine which patients are progressing slowly and which are moving along quickly and adjust treatment accordingly. With this information, extended hospital LOS due to ileus may be minimized and optimal treatment of non-ileus patients may allow accelerated discharge. Further, with a definitive signal of motor activity in each major GI organ, the confidence staff has in recommending discharge may be greater than currently obtained by monitoring flatus and bowel movements. As a result, the incidence of hospital readmission may decrease.

SUMMARY

Various embodiments provided herein overcome one or more of the shortcomings of previous systems and methods for monitoring and evaluating GI tract motor activity in post-surgical patients. Some embodiments provided herein include systems and methods for diagnosing or monitoring post-operative ileus (POI).

One aspect of the present disclosure is directed to a method of detecting resumption m motility within a stomach, a small intestine, and a colon of a patient following a surgical procedure. In some embodiments the method includes: placing a surface electrode patch onto an abdominal region of a patient; acquiring, by the surface electrode patch, an acquired signal comprising a myoelectrical activity signal; digitizing the acquired signal with an analog-to-digital converter present on the surface electrode patch; wirelessly transmitting the digitized signal to a computing device; automatically applying a time-stamp to the digitized signal; automatically distinguishing an activity level of each gastrointestinal organ from the time-stamped signal; and monitoring the activity level of each gastrointestinal organ to identify a change in activity level indicative of a resumption of motor activity M each of the gastrointestinal organs.

In some embodiments, the surface electrode patch includes a plurality of electrodes and electronic components. In some embodiments, the surface electrode patch is positioned on the patient following a surgical procedure. In some embodiments, the surface electrode patch is placed on the patient and positioned so as to avoid a surgical incision or wound.

In some embodiments, the activity level of each gastrointestinal organ is distinguished by one Or more of dividing a frequency spectrum of the time-stamped signal into a plurality of organ-specific; spectral regions, such that a first region corresponds to the stomach, a second region corresponds to the small intestine, and a third region corresponds to the colon; and summing or integrating the frequency spectrum of the time-stamped signal across each of the plurality of organ-specific spectral regions for a desired time duration, such that a resultant value as a function of time serves as a representation of a motor activity of the gastrointestinal organ associated with the organ-specific spectral region.

In some such embodiments, the first region in 2 to 4 cpm, the second region is 5 to 12 cpm, and the third region is >12 to 40 cpm.

In some embodiments, monitoring the activity level of each gastrointestinal organ begins in a clinical setting and continues following patient discharge.

In some embodiments, the patient is diagnosed with post-operative ileus if one or more of the gastrointestinal organs do not experience the change in activity level indicative of a resumption of motor activity within an expected timeframe. In some such embodiments, the expected timeframe is within 120 hours following the surgical procedure.

In some embodiments, the method includes calculating a post-operative ileus likelihood predictor (POILP). In some embodiments, the POILP assesses chances that the patient will need to stay in a hospital longer than average due to post-operative ileus, in some embodiments, the POILP is calculated based on a model comparing the time-stamped signal to prior patient signals, the prior patient signals associated with known prior patient outcomes.

In some embodiments, the method includes performing one or more of revising the POILP, raising a POILP reliability indicator, and narrowing a corresponding confidence interval as a patient reaches or fails to reach one or more expected milestones.

In some embodiments, the method includes comparing the time-stamped signal to prior patient signals acquired from past patients sharing similar demographic traits as the patient. In some such embodiments, the demographic traits include one or more of: age, weight, gender, race, overall health status, and type of surgery.

In some embodiments, the method includes receiving a patient input regarding, one or more of: a time of a meal, a time of an activity, a time of taking a medication, a time of a bowel movement, a time of nausea, a time of vomiting, and a time of pain; and correlating the patient input with the change in activity level of each gastrointestinal organ.

In some embodiments, the method includes calculating a background based on values well removed from a series of peaks in the frequency spectra; and subtracting the background from the frequency spectra to produce a net spectral activity value, in some embodiments, the series of peaks either reside within or outside a spectral region of interest or, are identified based on a general shape of the background In some embodiments, the method includes identifying a pattern indicative a blockage in one or more gastrointestinal organs.

In some embodiments, the method includes assessing a spectral energy across the frequency spectrum for a given time period; identifying elevated spectral energy as an artifact; and removing the artifact. In some such embodiments, spectral energy is an area under a curve of a frequency spectra peak integrated over a duration of the peak.

In some embodiments, the method includes scaling a strength of the acquired signal due to coupling at a skin surface of the patient and conduction through a body of the patient.

In some embodiments, the frequency spectra during periods of sleep are used as a background or baseline to evaluate the frequency spectra during wakefulness.

In some embodiments, the method includes representing the activity level of each gastrointestinal organ as a percentage of a time there was motor activity above a given threshold for each gastrointestinal organ.

In some embodiments, the method includes identifying and quantifying known gastrointestinal motility patterns in the frequency spectra of each gastrointestinal organ; and associating the known gastrointestinal motility patterns with known physiological patterns in each of the GI organs.

In some embodiments, the method includes predicting a likelihood of one or more of a bowel movement, flatus, nausea, and vomiting occurring in a specified time period based on the activity level of each of the gastrointestinal organs recorded up to a current moment.

In some embodiments, the method further includes administering a therapy to the patient; and monitoring the activity level of each gastrointestinal organ to determine whether the change in activity level occurs during or after administration of the therapy.

In some embodiments, the method includes alerting the patient to an increase in activity level of one or more of the gastrointestinal organs to encourage the patient to attempt a bowel movement.

Another aspect of the present disclosure is directed to a system for acquiring and processing myoelectrical data from the gastrointestinal tract representative of motor activity from a patient recovering from abdominal or thoracic surgery. In some embodiments, the system includes: a set of one or more wireless electrode patches; a computing device communicatively coupled (e.g., via a low energy wireless protocol) to the set of the one or more wireless electrode; and a processor communicatively coupled to the computing device and configured to process the raw myoelectrical data obtained from the set of one or more wireless electrode patches to provide quantitative and qualitative information on a motor activity of one or more gastrointestinal organs. In some such embodiments, the system functions to assess a health status of each gastrointestinal organ, in particular a recovery from a normal, temporary cessation of motor activity caused by surgery. In some embodiments, the system further function to communicate the results and other relevant information to a healthcare provider or caregiver, for example via a dedicated application on the computing device or via a web browser interface. In some embodiments, the system optionally includes a server to which the computing device is communicatively coupled, as least periodically.

In some embodiments, the set of one or more wireless electrodes patches are placed on an abdomen of the patient shortly after surgery, for example within a few hours after the patient has left the recovery area.

In some embodiments, the raw myoelectrical data is time stamped so as to account for gaps in the data due to breakdowns in wireless transmission, temporary or intermittent failures of a patch or computing device operation, or other reasons for the existence of missing data.

In some embodiments, external events such as meals, therapies, patient activity, and bowel movements are recorded with a time stamp in an application on the computing device and uploaded along with the raw myoelectrical data for inclusion in a data analysis. In some embodiments, the external events are recorded separately and later added to the data analysis.

In some embodiments, the data analysis is performed on a server and downloaded to a local computing device for viewing and interpretation, by a healthcare provider.

In some embodiments, the data analysis is performed on a local computing device for viewing and interpretation by a healthcare provider.

In some embodiments, a graphical user interface presented to a healthcare provider is displayed on a networked computing device. In some embodiments, the graphical user interface is updated continually as data is acquired and processed, typically within minutes. In some embodiments, the graphical user interface includes graphic and tabular information conveying a patient's previous and current activity level since beginning the test. In some embodiments, graphic information may include charts of the current and summed activity over time of each gastrointestinal organ. In some embodiments, the tabular information may include responses to external events.

In some embodiments, the graphical user interface is customizable to various overall levels of detail and various items of interest healthcare provider or caregiver.

In some embodiments, motor activity responses to therapies and interventions (e.g., gum walking or other exercise, etc.) are explicitly reported.

In some embodiments, the system may be further configured to send alerts via email, text messages and the like to a healthcare provider to indicate a set of user-selectable events. In some embodiments, such user-selectable events include motor activity in any organ above a given threshold indicating healthy recovery status, below a given level for a given amount of time indicating the possibility of relapse, changes in average level beyond a given threshold indicating either of the preceding, or other information of interest provided by the system.

In some embodiments, an alert is transmitted from the computing device via email, text message, etc. to alert a healthcare provider about system maintenance items (e.g., lost connections, low battery, etc.).

In some embodiments, the raw myoelectrical data is subjected to a procedure for removal of artifacts resulting from electrode malfunction, patient motion, breathing, skeletal muscle activity, etc.

In some embodiments, the data analysis includes calculation of frequency spectra in selected time intervals on an ongoing basis as the data is being, acquired, with the possibility of multiple such calculations using different intervals being carried out simultaneously. In some such embodiments, the time interval is between one and thirty minutes in length.

In some embodiments, the data analysis includes an algorithmically driven search through the time series data for events that fit a known pattern indicative of motor activity, in some embodiments, such patterns are less visible above noise background in a frequency spectrum analysis but includes characteristics that can be parameterized and identified in the time series with higher signal to noise ratio than in the spectra.

In some embodiments, the frequency spectra are summed over time and frequency to provide a value for total spectral activity in the specified region of frequency and time.

In some embodiments, a background is subtracted from the spectra to produce a net spectral activity value, said background calculated based on values well removed from spectral peaks, either within the spectral region of interest or outside it, using knowledge of the general shape of the background from prior studies.

In some embodiments, the spectral data analysis includes separating the data into separate frequency bands corresponding to the stomach, small intestine, and colon; and calculating total and net activity values for each organ as a function of time.

In some embodiments, a peak detection algorithm is employed to identify peaks in the spectra over a specified frequency range and time period, arising from motor activity; quantifying the height, width and duration of said peaks; and calculating a peak volume as a measure of motor activity in the given frequency band and time period.

In some embodiments, the peak activity is assigned to any of the stomach, small intestine, or colon based on the peaks' central frequency, width, or characteristics of its time evolution.

In some embodiments, artifact reduction may include assessing the spectral energy across the full frequency range for a given time period, and recognizing that elevated energy across a broad frequency range, as opposed to being confined to distinct peaks, is a signature of artifacts rather than motor activity.

In some embodiments, the raw myoelectrical data is scaled for signal strength due to coupling at the skin and conduction through the body.

In some embodiments, the frequency spectra data during periods of sleep are used as a background or baseline to evaluate the spectra during wakefulness.

In some embodiments, the data analysis includes correlating the activity levels and in particular the changes in activity levels with external events entered into the system (e.g., drinking or eating, gum chewing, physical activity, pain, and any other enterable item).

In some embodiments, the results are normalized against standards to present a comparative value, including normalization within a specific subgroup of patients that have similar characteristics to the patient under test, such as age, height, weight, ethnicity, surgery type, etc.

In some embodiments, the data analysis includes a representation of the percentage of the time when there was motor activity above a given threshold for each organ. In some such embodiments, the data analysis occurs up to a current moment. Alternatively, in some such embodiments, the data analysis includes specific time periods, such as during wakefulness or sleeping, the postprandial period immediately after meals, quiescent time periods between meals, etc.

In some embodiments, the data analysis includes identifying known gastrointestinal motility patterns such as the migrating motor complex (MMC) in the small intestine or the giant migrating contraction (GMC) in the colon; and evaluating their strength, duration, and number.

In some embodiments, the data analysis includes evaluating the response of a patient's heart rate to ingestion of fluids and meals.

In some embodiments, the data analysis includes a prediction of a likelihood of a bowel movement occurring in a specified next few hours based on the motor activity of the digestive organs recorded up to a current moment.

In some embodiments, the data analysis includes results of a calculation that estimates the likelihood of the patient developing post-operative item, leading to an extended hospital LOS. In some such embodiments, the data analysis takes into account the levels of activity of each organ, the pattern of such activity, responses to external stimuli, the difference between waking and sleeping activity, and so forth.

In some embodiments, the data analysis includes results of a calculation that estimates a likelihood of a patient being readmitted to a hospital after discharge. In some embodiments, the data analysis includes a level of activity of each organ, the pattern of such activity, responses to external stimuli, the difference between waking and sleeping activity, and so forth.

In some embodiments, the system may be adapted for use at home after discharge from a hospital, in which a patient continues wearing one or more electrode patches or has fresh patches applied. In some such embodiments, the computing device remains with the patient, data from the computing device continues to be uploaded to a server via an available network outside a hospital setting, and the results of the analysis continue to be shown to a healthcare provider, either the same group that has been monitoring the patient in the hospital or another group focused on such patient handoffs. In some such embodiments, the system is intended to continue monitoring the patient to ensure that recovery continues to proceed along an expected path, minimizing a chance of readmission with complications and possibly thereby allowing modestly earlier hospital discharge.

In some embodiments, the system is configured to provide a recommendation on possible therapeutic interventions based on the recorded motor activity and related information.

In some embodiments, the system is configured to alert the patient when increases in motor activity are detected as biofeedback, to encourage them to take advantage of the activity by attempting a bowel movement.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

The illustrated embodiments are merely examples and are not intended to limit the disclosure. The schematics are drawn to illustrate features and concepts and are not necessarily drawn to scale.

DETAILED DESCRIPTION

The provided figures and the following description of certain embodiments of the invention are not intended to limit the invention to these embodiments, but rather, are provided to enable any person skilled in the art to make and use this invention. Disclosed herein are various embodiments of wireless electrode patch systems configured to monitor GE motor activity in post-surgical patients. Related methods, described herein, have been developed to inform post-operative treatment, test the effectiveness of post-operative therapies, determine an appropriate time for hospital discharge, and accurately diagnose post-operative ileus.

Introduction

Figure 1:
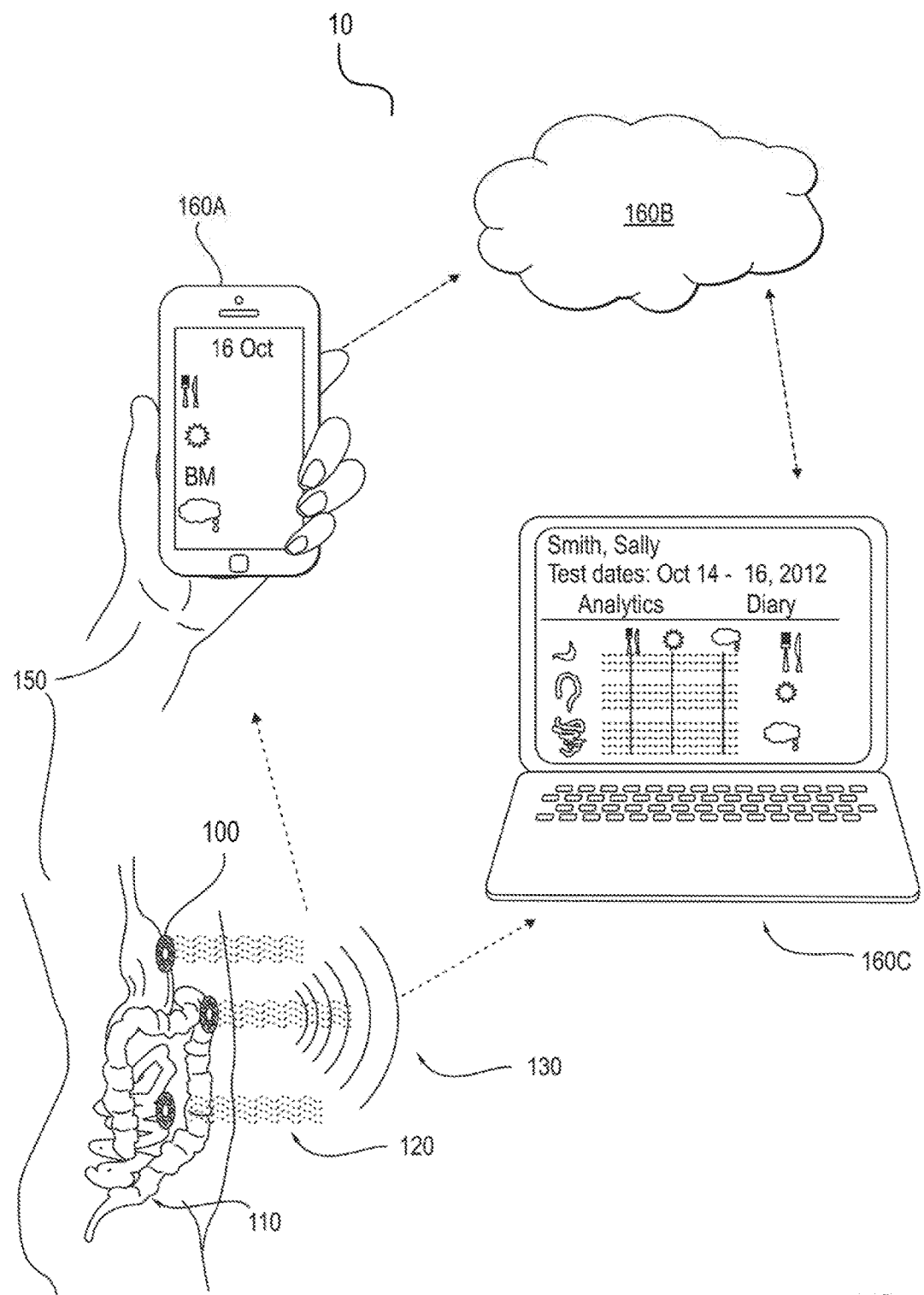
FIG. 1 illustrates schematically one embodiment of a system for detecting gastrointestinal motor activity.

One means of monitoring the gastrointestinal system noninvasively is shown in FIG. 1 and involves use of wireless electrode patches 100 attached to the abdomen, as described in U.S. patent application Ser. No. 14/051,440, entitled "Wearable Wireless Patches Containing Electrode Pair Arrays", the disclosure of which is herein incorporated by reference in its entirety. Such patches 100 acquire myoelectrical data in the form of voltage recordings that directly represent myoelectric activity of the digestive organs. The myoelectric activity of the digestive organs is known to relate to muscular activity (i.e., motor activity). Such wireless patches 100, designed for fully mobile patients at home, are easily worn by hospitalized patients without discomfort or otherwise interfering with any of their activities. The patches 100 record the myoelectrical signals 120 at the skin surface and transfer the readings to a mobile device 160A such as a smartphone, tablet, laptop, portable computer, wearable computing device, or iPod Touch type device. In some embodiments, the mobile device 160A uploads the readings to a cloud server 160B for further processing, while also allowing the patient 150 or caregiver to enter events such as pain, meals, bowel movements or urges, flatus, etc. In other embodiments, the further processing may also be performed on the mobile device 160A. The further processing step is performed with a computer application using algorithms that identify and quantify signals related to motor activity of each organ, and in some embodiments, blockage in an organ. For example, the system may detect or infer a blockage Wan upstream gastrointestinal organ (e.g., small intestine) is exhibiting increased motor activity, while a downstream gastrointestinal organ (e.g., colon) is exhibiting reduced motor activity.

It is the insight of the inventors of the present technology that using a modified system of wireless electrode patches 100, as shown in FIG. 1, to record and evaluate motor activity from the GI tract 110 on post-surgical patients during recovery would be a valuable tool, enabling medical staff to determine the rate of recovery of the digestive system. It may enable accelerated discharge from the hospital for patients progressing faster than average, and it may help identify those who are at risk of developing post-operative ileus, enabling earlier intervention. In both situations, there is the potential to reduce hospital LOS, thereby benefiting the patient, hospital, and healthcare system.

Some embodiments of such a system of wireless electrode patches and related methods of monitoring and diagnosis are provided herein.

Systems

Figure 2:
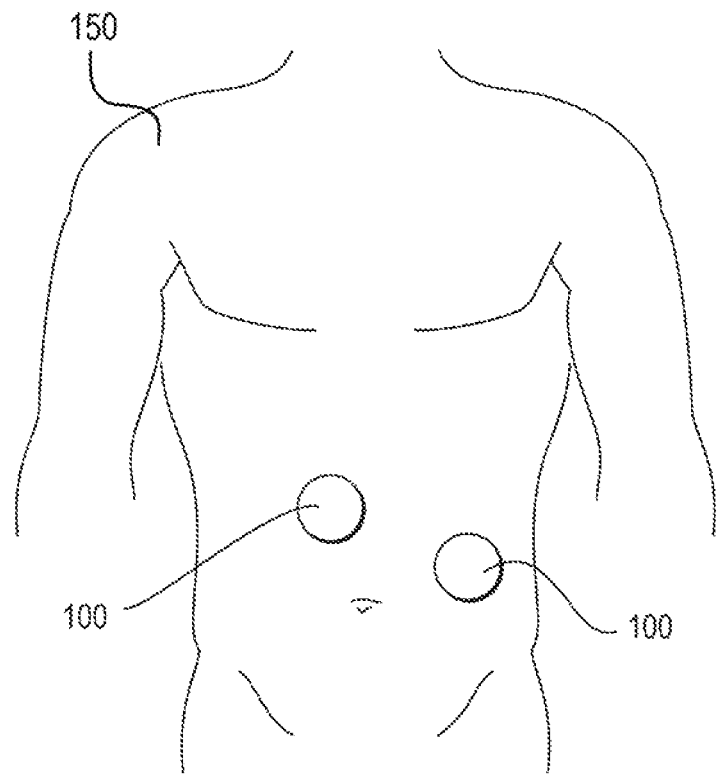
FIG. 2 illustrates one embodiment of a patch for detecting gastrointestinal motor activity.

One embodiment of a wireless electrode patch system 10 in accordance with the present disclosure is shown in FIGS. 1-2. In the depicted embodiment, the wireless electrode patch system 10 includes one or more patches 100 communicating with a mobile device 160A such as a smartphone, wearable device, or other portable computing device, using a low energy protocol 130 such as Bluetooth LE, as also described in U.S. patent application Ser. No. 14/051,440. The system 10 also includes a cloud-based server 160B for storage of data uploaded by the mobile device 160A via standard protocols 130 such as Wi-Fi or cellular phone connections. Processing occurs on the mobile device 160A, in the cloud 160B, or on a separate communicatively coupled computing device 160C to provide information related to the motor activity of the GI tract 110. As shown in FIGS. 2 and 4A-4E, the patches 100 have one or more sets of electrodes 205 that are in contact with the skin on the abdominal region of a patient 150.

Figure 4A:
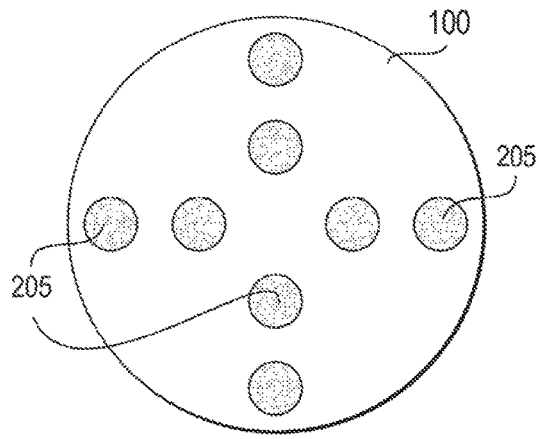
FIG. 4A illustrates one embodiment of an electrode configuration of a patch for detecting gastrointestinal motor activity.
Figure 4B:
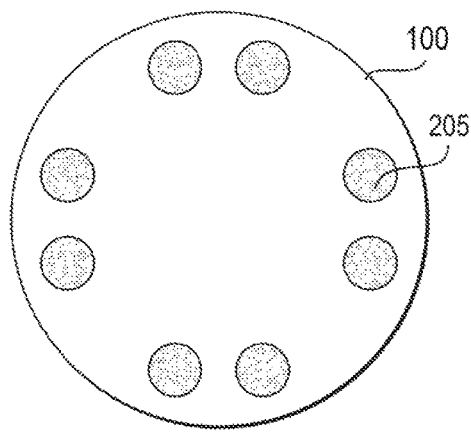
FIG. 4B illustrates another embodiment of an electrode configuration of a patch for detecting gastrointestinal motor activity.
Figure 4C:
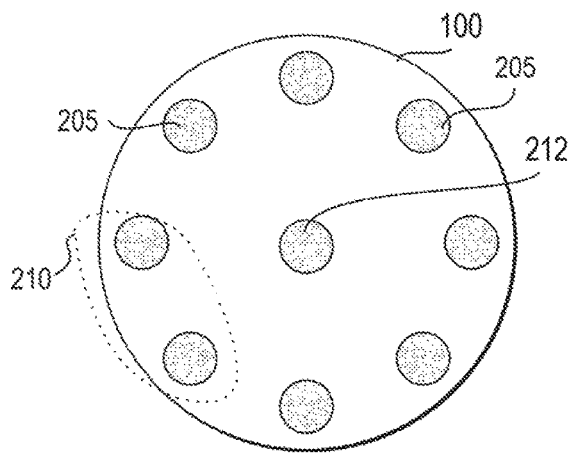
FIG. 4C illustrates another embodiment of an electrode configuration of a patch for detecting gastrointestinal motor activity.

As shown in FIGS. 4A-4D, pairs 210 of bipolar electrodes 205 may be arranged in geometric schemes. In some embodiments, a particular type of geometric scheme may make it possible to determine the direction from which a signal is emanating, and to estimate its strength and breadth more accurately than a single measurement point or pair of electrodes. For example, in some embodiments, at least two parallel pairs 210 of electrodes 205 are provided, as shown in FIGS. 4B-4C. In some such embodiments, a direction may be inferred by measuring a relative signal strength observed on the separate parallel pairs of electrodes. For example, if the signal is stronger on a first electrode pair than a second electrode pair, then the signal likely originated closer to the first electrode pair. Further, in some embodiments, as shown in FIGS. 4A-4C, at least four pairs 210 of electrodes 205 are provided such that each pair of electrodes is parallel to or aligned with another pair of electrodes and perpendicular to at least one other pair of electrodes. In some such embodiments, the ratio of signal strength between electrode pairs 210 can be used to determine direction of the source of the signal at any angular orientation in a two dimensional plane.

In some embodiments, pairs of signals also provide the opportunity to distinguish between artifacts or noise in a single channel and real physiological, signals that are identified in multiple channels. For example, real physiological signals are likely to follow certain patterns in terms of the ratio of strength among multiple channels. Signals that appear on only a single channel and signals that appear more or less equally on all of the parallel and perpendicular channels are more likely to be artifacts or noise.

Figure 3:
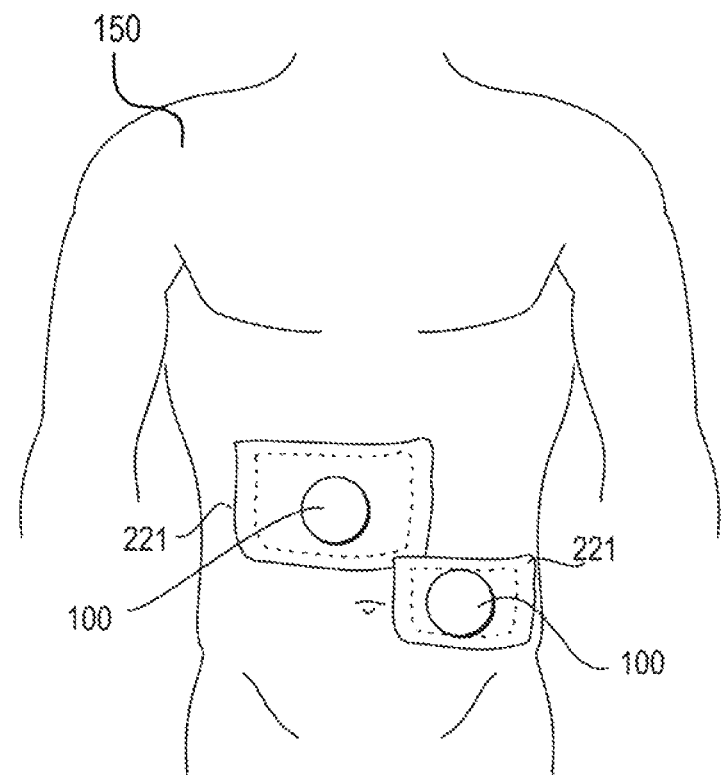
FIG. 3 illustrates one embodiment of a patch, incorporated into a bandage or wound dressing, for detecting gastrointestinal motor activity.

The patches 100 of some embodiments are sufficiently small so as to able arrangement on various locations of the abdominal region while avoiding surgical incisions and wounds, as shown in FIG. 2. Alternatively, in some embodiments, a surgical dressing or bandage 221 includes the patch 100 comprising the surface electrodes, as shown in FIG. 3.

In some embodiments, the patches 100 are sized such that one, two, three, four, five, or more patches 100 cart fit on an abdomen of a patient 150. In some embodiments, only two patches 100 need to be positioned on a patient 150 to properly monitor the myoelectrical activity of the GI system. An example placement of the patches 100 on a patient 150 is shown in FIG. 2. In other embodiments, only one patch 100 is needed; in some embodiments, three patches 100 are recommended.

Figure 4D:
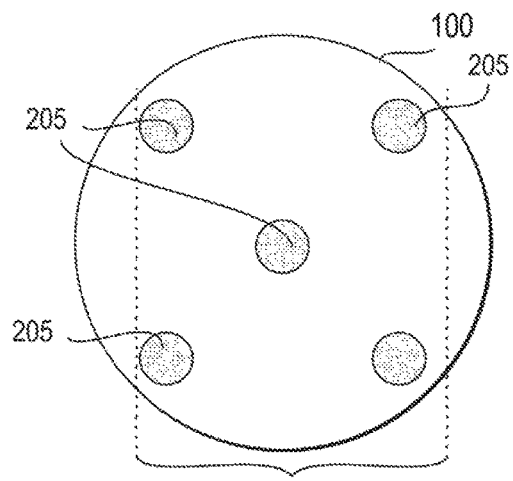
FIG. 4D illustrates another embodiment of an electrode configuration of a patch for detecting gastrointestinal motor activity.
Figure 4E:
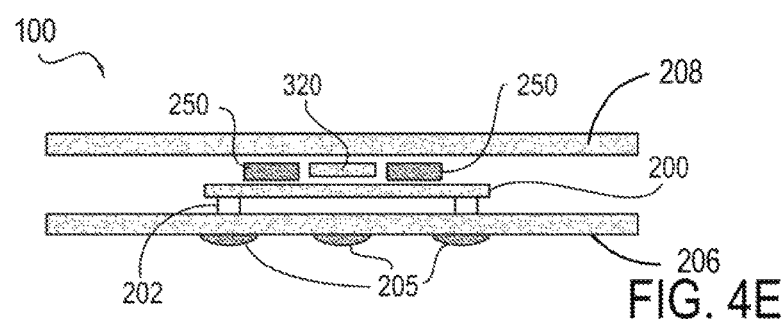
FIG. 4E illustrates a side view of one embodiment of a patch for detecting gastrointestinal motor activity.

One embodiment of a patch design and several non-limiting examples of electrode configurations are provided in FIGS. 4A-4E. As shown in FIG. 4E, the patch 100 of some embodiments includes a bottom, skin-side layer 206 with two or more bipolar electrode pairs 210 positioned on a bottom surface of the bottom layer 206. A plurality of integrated circuit (IC) board adhesive pins 202 extend through the bottom layer 206 to connect each electrode 205 of the bipolar electrode pairs 210 to an integrated circuit board 200 positioned on a top surface of the bottom layer 206. In some embodiments, the electronics of the integrated circuit board 200 are protected from moisture and patient manipulation by being sandwiched between a waterproof top, air-side layer 208 and the bottom, skin-side layer 206. The integrated circuit board 200 includes one or more integrated circuits 250 and a battery 320. The integrated circuit board 200 may also include signal processing components. For example, the integrated circuit board 200 may include one or more of: a filter (e.g., low pass filter, high pass filter, or band pass filter), an amplifier, an analog-to-digital converter (ADC), and a processor (e.g., Arduino® or other microcontroller) to process and analyze signals received from the electrodes 205. The patch 100 may further include a transmitter or a transceiver antenna to transmit signals from the patch 100 to the cloud-based server 160B or the mobile device 160A, as shown in FIG. 1.

In some embodiments, as shown in FIGS. 4A-4D, each patch 100 includes two, three, four, five, six, seven, eight, nine, ten, or more electrodes 205. In one embodiment, the patch 100 includes four bipolar electrode pairs 210, for example as shown in FIGS. 4A-4C. In some such embodiments, the patch 100 also includes a grounding electrode 212 for a total of nine electrodes 205. Further, in some embodiments, a plurality of interchangeably paired electrodes 205 may form an electrode array 220, as shown in FIG. 4D. In some such embodiments in which the electrodes 205 are configured to change the pairings of electrodes during signal acquisition, fewer electrodes may be needed to determine directionality, strength, and/or breadth of the signal. While a few example electrode arrangements are shown in FIGS. 4A-4D, those skilled in the art will appreciate that any suitable electrode arrangement may be used and is contemplated herein. Moreover, while a circular patch is shown, it is also contemplated that the patch may be rectangular, star shaped, oval, or any other suitable regular or irregular shape.

The patches 100 of some embodiments contain sufficient on-board memory to enable storage of raw data to reduce the need to maintain a continuous connection with the mobile device 160A, thereby conserving battery power and enabling data buffering so data is not lost when a connection is unavailable. Data may be stored in the on-board memory for a brief period such as minutes, an intermediate period such as hours, or the entire test period, which may be several days. The storage may be of a nonvolatile type, so that even if the battery 320 has been exhausted, a fresh source of power will allow retrieval of the stored data.

The mobile device 160A of some embodiments receives the raw data from the patch 100 via a low energy protocol such as Bluetooth LE, Bluetooth 4.1, or an equivalent or more modern protocol. The mobile device 160A of various embodiments has a graphical user interface (GUI) that allows setup of the system, entering of identification information (whether in coded format compatible with HIPAA or not), communication pairing with the patch 100, and so forth. The GUI 180 is configured to receive user input information such as information regarding when a patient experienced pain, drank, ate, took medications, visited the bathroom, exercised, had flatus, experienced nausea, vomited, or engaged in any other activity relevant to the patient's health in the context of the test, as shown in FIG. 7.

In some embodiments, the raw data or minimally processed data is uploaded by the mobile device 160A using Wi-Fi, cellular communications, or similar technologies to the cloud-based server 160B where it is stored, and optionally, processed further. Further processing, whether performed on a cloud-based server 160B, on the mobile device 160A, or on another communicatively coupled computing device 160C, involves extraction of signals indicative of motor activity of the Major digestive organs, including the stomach, small intestine, and colon. The processed results may be expressed in a multitude of presentation formats that may be made available to the attending medical professionals via a web-based interface, through a mobile application on a mobile computing device, or an application running on a notebook or desktop computing device. The results of some embodiments are available in a real-time mode, in which the latest data is typically updated within minutes, depending on details of the data analysis.

Figure 5:
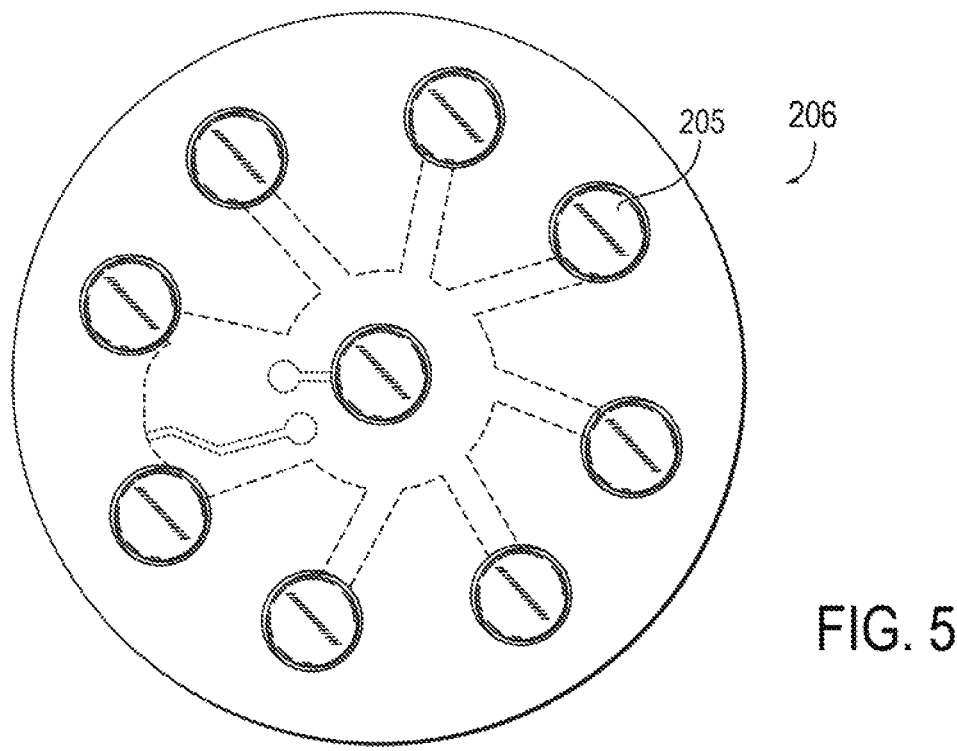
FIG. 5 illustrates a bottom view of one embodiment of a patch for detecting gastrointestinal motor activity.
Figure 6:
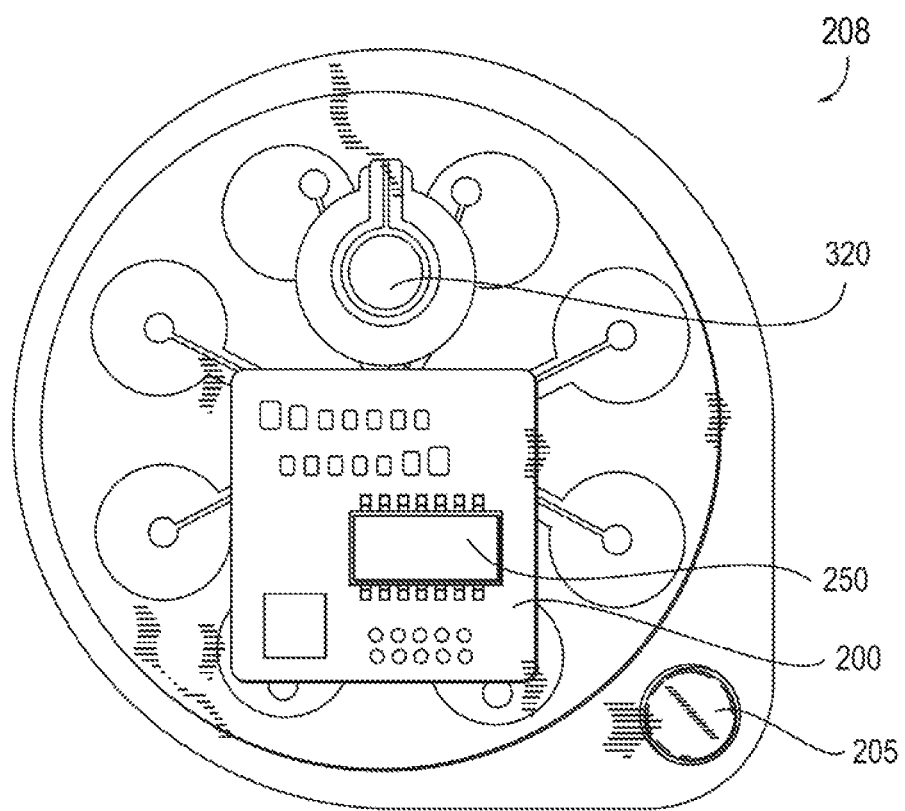
FIG. 6 illustrates a top view of one embodiment of a patch for detecting gastrointestinal motor activity with a top cover removed or shown transparently.

FIGS. 4-5 show, respectively, a bottom view 206 and a top view 208 of another non-limiting example of a wireless electrode patch 100. The electrode patch 100 functions to myoelectrical data in the form of voltage readings that represent electrical activity of the gastrointestinal organs. For long-term non-invasive GI tract monitoring, an inexpensive, light, water-resistant, and disposable skin-adhesive unit is provided. Because the unit is disposable, it can be easily replaced with another disposable unit after its usage for a period of time (e.g., hours, days, weeks). In some embodiments, the bottom 206 of the disposable unit has an adhesive surface that can be affixed to the patient's skin for 7-14 days. In one embodiment, the bottom 206 of the disposable unit can be affixed to the patient's skin for at least 7 days. In some embodiments, the adhesive includes a drying adhesive (e.g., white glue, rubber cement, contact adhesives), pressure-sensitive adhesive, contact adhesive (e.g., natural rubber, neoprene), hot adhesive (e.g., hot glue), or multi-part adhesive e.g., Polyester resin and polyurethane resin, polyols and polyurethane resin, acrylic polymers and polyurethane resins). In one embodiment, the adhesive is a pressure-sensitive adhesive, which forms a bond when pressure is applied to stick the adhesive to the adherent (e.g., the patient's skin). Further, as shown in FIG. 5, the patch 100 includes pairs of bipolar electrode 205 on the bottom surface 206. The top surface 208, as shown in FIG. 6, includes a printed circuit board 200 and a power source 320. The printed circuit board 200 and power source 320 may be protected from moisture or user movement by an additional layer that couples to the bottom surface 206 and sandwiches the printed circuit board 200 and power source 320 between the bottom layer 206 and a top layer 208, as shown in FIG. 4E.

Figure 7:
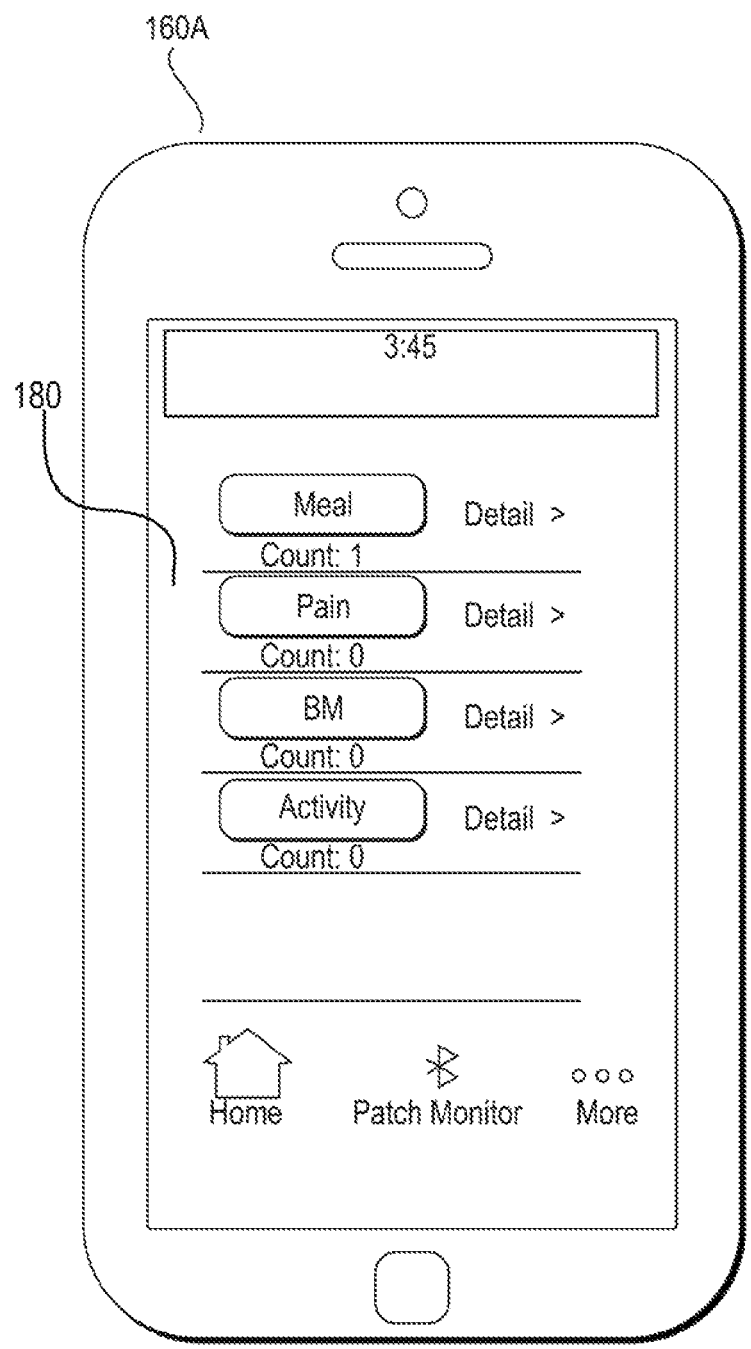
FIG. 7 illustrates one embodiment of a graphical user interface on a computing device for receiving one or more user inputs.

One non-limiting example of the mobile application GUI 180 is provided in FIG. 7. The GUI 180 on the mobile device 160A functions to receive user input related to external events that may affect a functioning of one or more gastrointestinal organs. The external events may be correlated with the signals seen in the data acquired from one or more patches. Non-limiting examples of external events include: meal or liquid consumption (i.e., Meal), pain episodes (i.e., Pain), bowel movement (i.e., BM), physical activity (i.e., Activity), meal or liquid consumption, nausea episodes, vomiting, flatus, or other external events may be recorded using the GUI 180. A user may input the external event using a drop down menu, a text box, by selecting a button that counts up a digital counter when selected, or by any other interaction with the GUI 180.

Data Features

Figure 8:
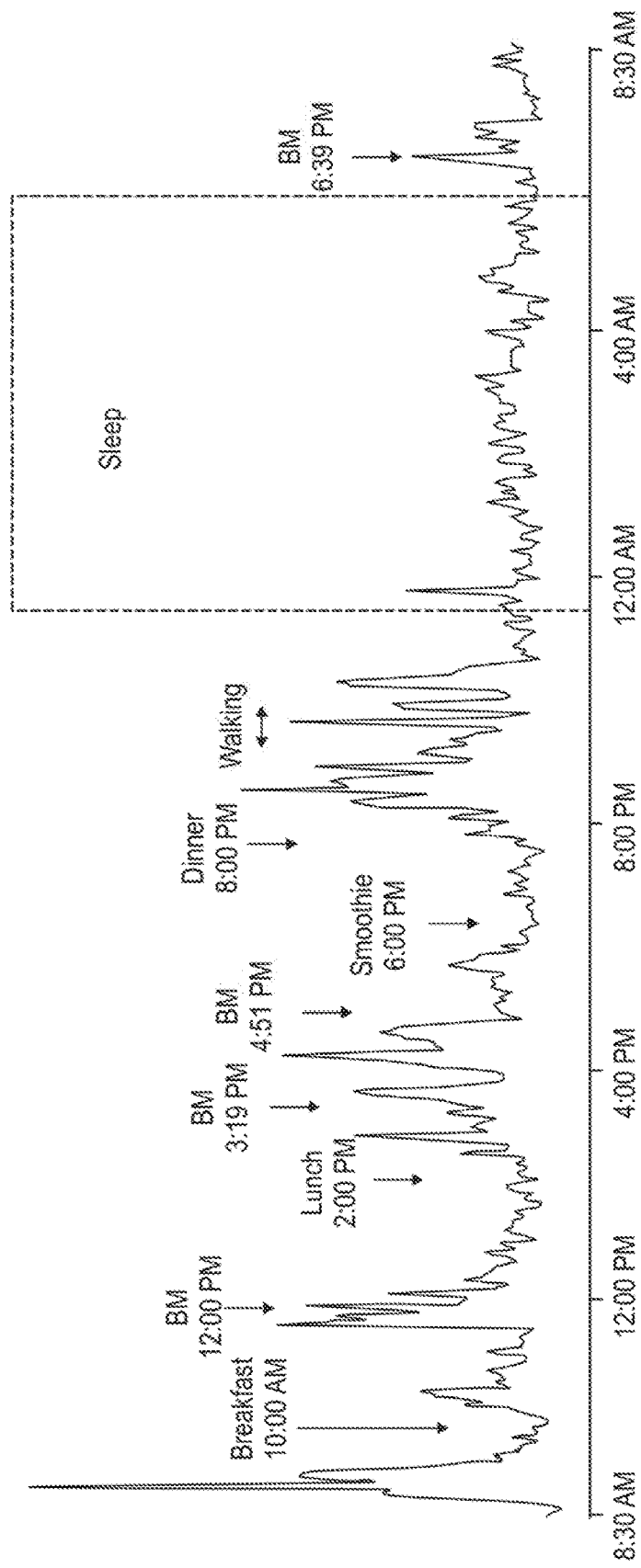
FIG. 8 shows cleaned example data representing gastrointestinal motor activity over a twenty-four hour period.

Embodiments of the electrode patch system acquire raw time series data, which include; large amplitude bursts that are artifacts of the collection process, gaps due to transmission lapses, and random slow drift. All these features of the raw data add to the challenges of extracting meaningful information from the signal. In the raw data view, the information of interest is not visible, International PCT Appl. No. PCT/US2015/056282 entitled "Systems and Methods for Processing Electromyographic Signals of the Gastrointestinal Tract", which is herein incorporated by reference in its entirety, describes the process of removing artifacts, filtering, and compensating for variations in signal strength between patients. Algorithms for performing such functions are also provided therein. In various embodiments provided herein, at least one computer of the electrode patch system (e.g., the mobile device, cloud server, or other connected computer) is configured to perform some of or all the steps of removing artifacts, filtering the signal, and compensating, for variations in signal strength between patients. An example of cleaned data, which may be produced by the computing devices of the electrode patch system, is shown in FIG. 8. As shown, there is random broadband noise but also periodic nearly sinusoidal variation that is linked to the myoelectrical activity that drives motor activity.

As described in U.S. patent application Ser. No. 14/051, 440 and International PCT Appl. No. PCT/US2015/056282 entitled "Systems and Methods for Processing Electromyographic Signals of the Gastrointestinal Tract", which are herein incorporated by reference in their entireties, conversion of the cleaned data (e.g., the data shown in FIG. 8) into frequency space spectra reveals peaks at several frequencies. In various embodiments of the electrode patch system, this conversion is performed by the server, mobile device, or connected computer via a technique such as the Fast Fourier Transform (FFT).

Figure 9A:
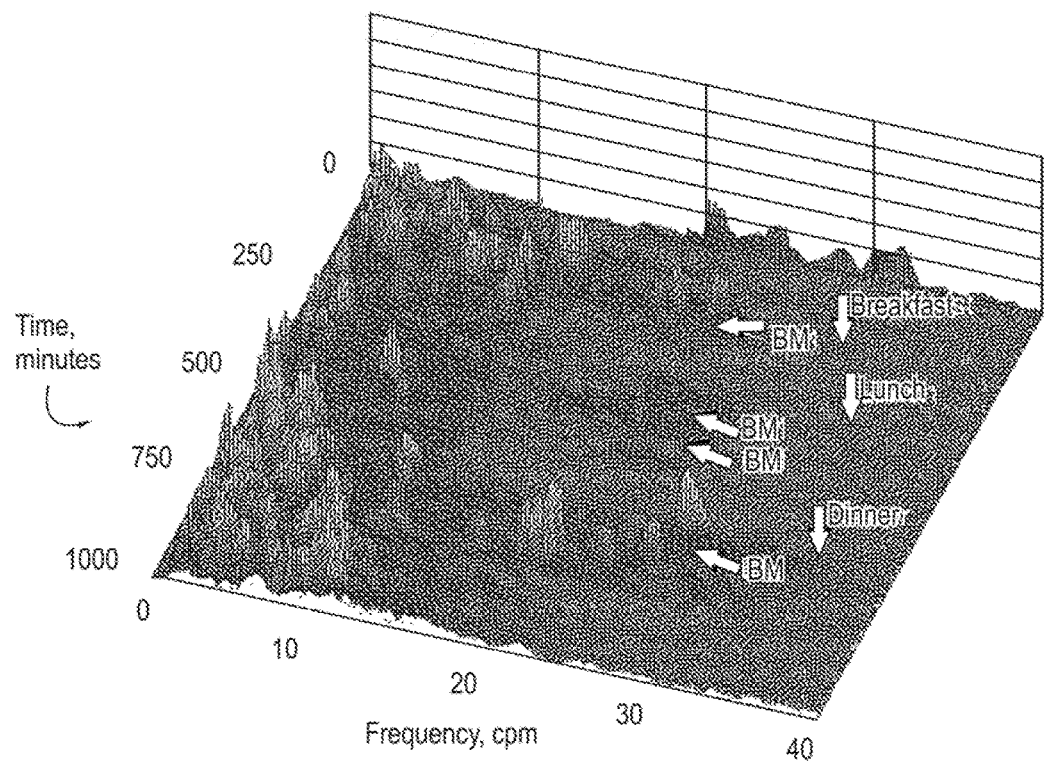
FIG. 9A shows example data in which peaks are visible at several frequencies, corresponding to emanations from specific gastrointestinal organs.
Figure 9B:
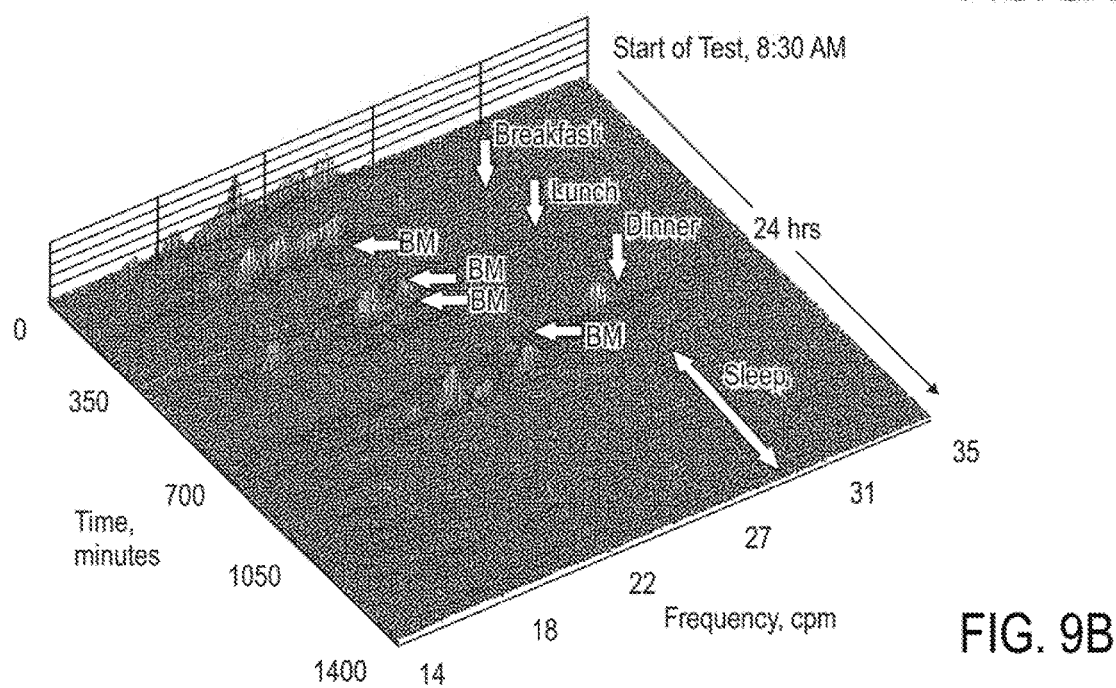
FIG. 9B shows example data in which peaks are visible at several frequencies, corresponding to emanations from specific digestive gastrointestinal organs relative to external events, for example meal times or sleep.

A representative spectrum is shown in FIGS. 9A and 9B, where peaks are visible at several frequencies, corresponding to emanations from specific digestive organs or particular user activities (e.g., a bowel movement (BM), meal, sleep, etc.), depending on the frequency. For example, the peak at 3 cpm is known to be from the stomach. Various embodiments of the electrode patch system, when used with any of the methods described herein, output frequency space spectra having peaks at several frequencies within the range of 1 to 40 cycles per minute (cpm). This frequency has been shown to correspond to rhythmic slow waves from the digestive organs. At frequencies from about 50 to about 90 cpm, most patients' primary heartbeat signal is manifested. Thus, in at least some embodiments, frequencies above about 50 cpm are ignored, and frequencies between about 1 and 40 eon are analyzed and classified to identify which GI organ or organs are experiencing motor activity (and thus generating myoelectric signals) at various points in time.

Methods

The system described in U.S. patent application Ser. No. 14/051,440 is oriented toward in-home use to determine causes of functional GI disorders. The electrode patch based system described herein may be used for other potential uses, including use in a hospital setting to monitor the level of motor activity of the major GI organs, including the stomach, small intestine, and colon, as they resume function following surgery. Such monitoring is particularly important following those types of surgery that involve incisions into, or manipulation of, the abdominal and thoracic cavities, which are known to affect function of the GI tract. When the digestive organs do not have normal function, the patient is said to have developed an ileus. Post-operative ileus (POI) is a term normally used to describe the cessation of function, particularly in cases where the lack of function goes on longer than expected, for example, greater than 24 hours, 48 hours, 72 hours, 96 hours, or 120 hours. For major abdominal surgery, the normal delay after surgery is three to four days, with the resumption of function signaled by the passage of gas (i.e., flatus) and/or of stool (i.e., defecation).

Figure 10:
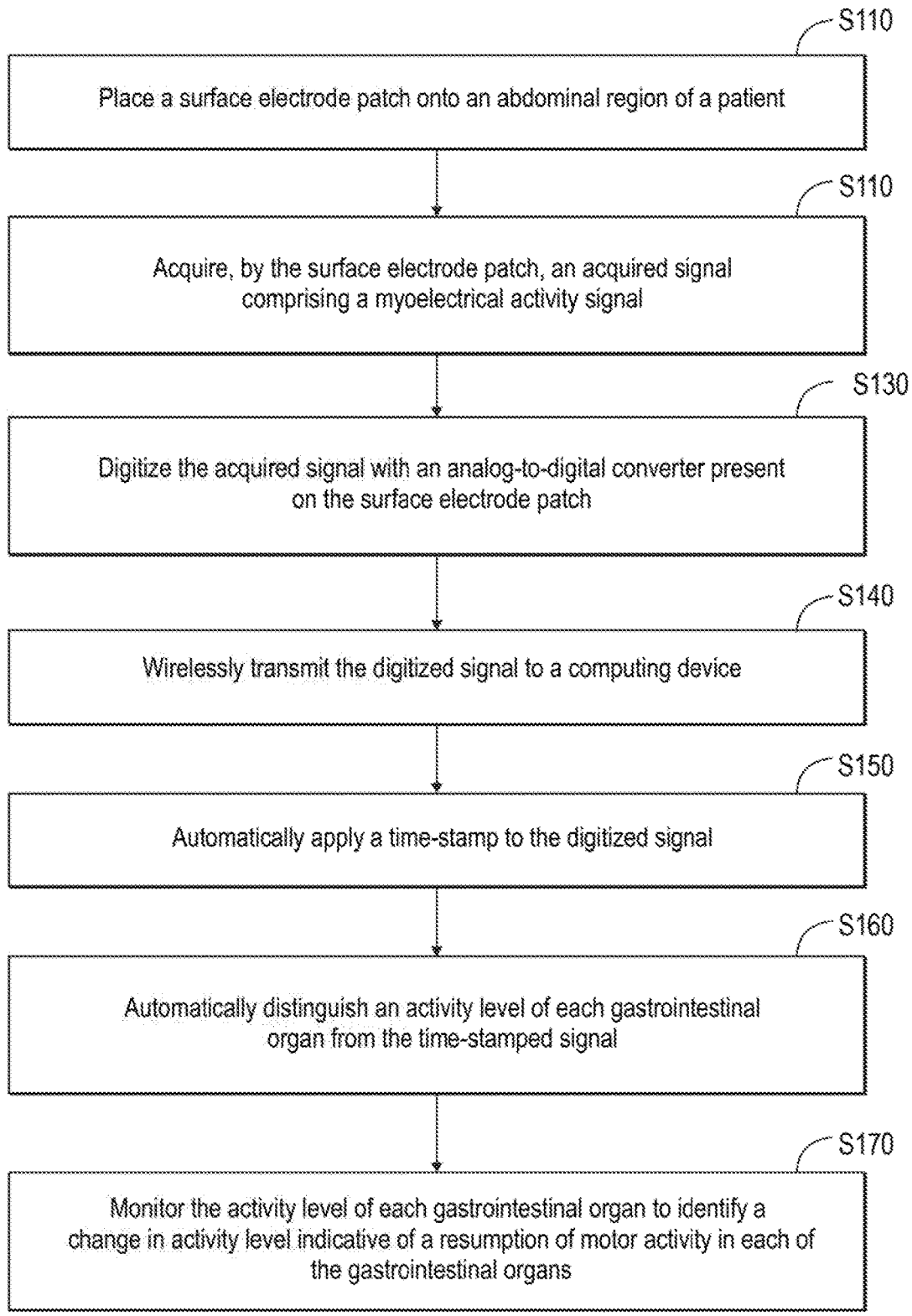
FIG. 10 is a flow chart of one embodiment of a method of detecting resumption in motility within one or more gastrointestinal organs.

As shown in FIG. 10, a method of detecting resumption in motility within a stomach, a small intestine, and a colon of a patient following a surgical procedure includes block S110, which recites placing a surface electrode patch onto an abdominal region of a patient. For use in postoperative recovery, the electrode patches such as any of the electrode patches described above) are placed shortly after surgery, in the operating room, the recovery room, or the patient's room, preferably within 12 hours of surgery. This allows the quiescent period before any of the organs resume motor activity to be identified and measured as a baseline. Typically, two to three patches are placed, depending on the size of the patient and the presence of surgical incisions, which should not be covered by the patches, unless the electrodes are integrated into the wound dressing or bandage.

As shown in FIG. 10, a method of detecting resumption in motility within a stomach, a small intestine, and a colon of a patient following a surgical procedure includes block S120, which recites by the surface electrode patch, an acquired signal comprising a myoelectrical activity signal. One or more electrode patches may be kept on the patient's skin over at least a portion of the gastrointestinal tract for one or more days. During this time, the one or more patches detect electromyography signals in real-time.

As shown in FIG. 10, a method of detecting resumption in motility within a stomach, a small intestine, and a colon of a patient following a surgical procedure includes block S130, which recites digitizing the acquired signal with an analog-to-digital converter present on the surface electrode patch. The electromyography signals detected by the one or more patches on the patient are amplified, filtered, and/or converted from analog signals to digital signals using signal processing components present on the integrated circuit board of the patch. The digital signals are transmitted from the patch to the mobile device via a beacon (e.g., for transmitting a unique identifier or data), Bluetooth LE, nearfield communications (NFC) antenna, or other wireless data transmitter.

As shown in FIG. 10, a method of detecting resumption in motility within a stomach, a small intestine, and a colon of a patient following a surgical procedure includes blocks S140 and S150, which recite wirelessly transmit the digitized signal to a computing device; and automatically apply a time-stamp to the digitized signal. Blocks S140 and S150 function as a way of correlating signals seen in the data with external events. Such external events, for example physical activity, meal or liquid consumption, pain episodes, nausea, vomiting, flatus, or bathroom visits may be recorded on the mobile device or another communicatively coupled computer by the patient or attending staff, and are similarly time-stamped.

In one embodiment, the mobile device transmits the raw digital data and recorded events to a cloud server via a wireless link such as Wi-Fi or a cellular radio, for processing and analysis. Results can be displayed on a display screen of a web capable device (e.g., computer or tablet), or in a dedicated application on a mobile device, tablet device, or computer. The nature of the application requires that the results be made available in a timely fashion, e.g., within one hour or less.

In another embodiment, either partial processing or full processing is performed on the mobile device, with results displayed nearly in real time, e.g., within seconds or minutes.

As shown in FIG. 10, a method of detecting resumption in motility within a stomach, a small intestine, and a colon of a patient following a surgical procedure includes block S160, which recites automatically distinguishing an activity level of each gastrointestinal organ from the time-stamped signal. The activity level of each gastrointestinal organ may be distinguished by one or more of: dividing a frequency spectrum of the time-stamped signal into a plurality of organ-specific spectral regions; and summing or integrating the frequency spectrum of the time-stamped signal across each of the plurality of organ-specific spectral regions for a desired time duration. A resultant value of the summing or integrating as a function of time serves as a representation of a motor activity of the gastrointestinal organ associated with the organ-specific spectral region. In some embodiments, the first region corresponds to the stomach, the second region corresponds to the small intestine, and the third region corresponds to the colon. Such methods are described in further detail elsewhere herein.

As shown in FIG. 10, a method of detecting resumption in motility within a stomach, a small intestine, and a colon of a patient following a surgical procedure includes block S170, which recites monitoring the activity level of each gastrointestinal organ to identify a change in activity level indicative of a resumption of motor activity in each of the gastrointestinal organs. In some embodiments, monitoring includes displaying the activity level to a user of the system, sending an alert to a user or the system, providing a recommendation to a user of the system, or updating a status of the user or a condition of the user. In some embodiments, the results displayed on a display screen include some or all of the following elements valuable to the caregiver in determining the patient's recovery status: the current activity level of each GI organ, integrated activity since beginning of test, and integrated activity in specific time periods (e.g., last hour, last 12 hours, etc.), on a universal, relative, or absolute scale. The same information may also be presented on a relative scale based on the patient's age, gender, height/weight/body mass index, type of surgery, ethnicity, or other factor capable of influencing the results in a predictable manner.

The results displayed in the user interface may be customizable so that the staff is able to decide which of the many results to show prominently, which to show as secondary items and which to hide from display. The customization interface provides tools to enable modification of the size and location of the included items. Typically, this is done as a general configuration step by a person with appropriate skills in advance of a patient test; in some embodiments, this configuration be modified during a patient test based on questions a caregiver has or results being generated; in still further embodiments, this configuration is set to a site-wide standard, which is not changed for every patient test.

In some embodiments, the system correlates measured motor activity to external recorded events as defined previously, with timely reporting of the level of response seen to each event in the user interface. For example, m some embodiments, a processed signal of motor activity over time is displayed in the user interface with recorded events flagged at the appropriate corresponding, time on the graph (as seen, for example, in FIG. 8). In this way, the caregiver and/or patient is able to see whether any of the activities have an effect on the GI tract. Such information helps inform treatment decisions, allowing the caregiver and/or patient to determine and plan further actions based on what has and has not been effective previously.

In some embodiments, the system delivers alerts on selected events or actions by text, email, or similar vehicle to a remote computing device. Additionally or alternatively, some embodiments, alerts are generated on the patient-side mobile device and include audible alarms, flashing lights, pop-up messages, notifications, or other similar alerts. For example, the detection of a sudden increase in motor activity in one of the digestive organs can be reported to the patient and/or caregiver, while the indication entered by the patient of pain or a bowel movement may be relayed automatically, for example, via a wireless transmission, to a computing device monitored by the caregiver team. In some embodiments, all such alerts are customizable.

Similarity, in some embodiments, alerts can be delivered pertaining to the operation of the patch system itself rather than the patient, such alerts including, for example, warnings of disconnection between patch and mobile device, low battery, evidence of poor performance implying damage to or partial removal of a patch, etc.

Data Processing

In a various embodiments, it is necessary to remove from the raw digital data stream artifacts resulting from electrode malfunction, electrode slippage, patient motion, breathing, or other skeletal muscle activity. Such artifacts induce much larger amplitude signals than from the underlying organ motor activity but are typically brief and have recognizable patterns that identify them as artifactual in origin. In some embodiments, the techniques detailed in International PCT Appl, No. PCT/US2015/056282 entitled "Systems and Methods for Processing Electromyographic Signals of the Gastrointestinal Tract", are used to remove such artifacts from the raw digital data. One non-limiting example of a method of extracting valid gastrointestinal tract electromyography data from a raw time series data set acquired from a skin-surface mounted electrode patch includes: identifying artifacts within the raw time series data, said identifiable artifacts comprising a set of data points nominally centered on a point of largest excursion from average value of zero-crossing and extending toward the average or zero-crossing; eliminating the identified artifacts by tracking them down to any of a zero-crossing or a midpoint-crossing point on either side of a high amplitude artifact; and replacing the artifacts with any of interpolated points or constant value points that span a gap across the eliminated artifacts to create a clean time series data set comprising valid gastrointestinal tract EMG signals. In some embodiments, the method further includes: modifying the raw time series data set to create a modified time series data set. For example, modifying may include filtering the data set to remove drill.

In some embodiments, processing the data involves applying the Fast Fourier Transform, (FFT) to determine the frequency spectrum characteristics. It is well known that motor activity in the digestive organs is associated with periodic or rhythmic activity, and this rhythmic activity is associated with electrical signals that can be measured at the skin surface. In particular, the data may be broken up into multiple time segments and a spectrum calculated for each time segment to discern the progression of the rhythmic signals over time. Identification and quantification of the peaks in, the spectra at frequencies associated with the stomach, small intestine and colon, as described in International PCT Appl. No. PCT/US2015/056282 entitled "Systems and Methods for Processing Electromyographic Signals of the Gastrointestinal Tract", is an effective means of identifying motor activity of each of the major digestive organs. In some embodiments, a method of identifying peaks in the frequency spectrum of a gastrointestinal EMG data set acquired from an electrode patch mounted on a skin surface of a patient includes: calculating a series of frequency spectra within the EMG data set using sequential time series segment subsets; and setting first and second thresholds based on a calculated spectrum within the acquired data.

A first threshold is applicable to identifying a background or baseline amplitude; a second threshold is higher than the first threshold, and is applicable for identifying peaks in the data set. Both first and second thresholds are determined based on values in the calculated spectrum within the data set. In some embodiments, the method further includes: locating points within the data set that are above the amplitude of the second threshold by way of a known peak detection algorithm to yield one or more identified peaks; applying a set of "cuts" to the one or more identified peaks; and calculating the volume above the baseline amplitude of each identified peak in each sequential time segment. In some embodiments, the method further includes: segregating the identified peaks into subsets based on any one or more of (1) predetermined frequency ranges associated with motor activity of specific gastrointestinal organs or (2) time periods as identified by patient activity; and summing the volumes of all peaks within the data subsets. The time periods referred to may include any diurnal aspect of the time during which data are acquired or any gastrointestinal event, such as eating a meal.

In some embodiments of the method, the first threshold is determined in terms of percentile rank of all the spectral data set points, and the peak threshold is based on a second, higher percentile rank. Further, in some embodiments, the background value and peak threshold are based on predetermined fixed percentages of the highest and lowest values.

In some embodiments of the method, the one or more known peak detection algorithms is any one or more of a simple threshold peak detector, a piecewise threshold peak detector, a peak detector that employs quadratic fits, a peak detector that imposes simple constraints such as requiring consecutive values above threshold, a peak detector that provides smoothing prior to peak detection, or any other suitable approach.

In some embodiments of the method, the cuts are based on any one or more of: absolute spectral amplitude values, on net amplitude values with background subtracted, on net amplitude values scaled in terms of the background value, on having a minimum distance in frequency units from an adjacent peak, on having a minimum distance from a boundary of the spectral region, and on having a structural shape such that the sides of the peak as they drop below the peak threshold continue to decrease to less than some specified fraction of the maximum value before again crossing the peak threshold, thereby establishing that the peaks are indeed separate.

In some embodiments of the method, the spectrum amplitudes are scaled by the frequency to improve the detection of higher frequency peaks that often have lower amplitude in a sub-range that may have more than one peak.

In some embodiments of the method, the spectral range is broken into several meaningful sub-ranges, with different sets of threshold, peak detection, and cut criteria control values in each, such sub-ranges representative of known physiologic activity, for example of activity from the stomach, small intestine, and the colon, where the summing or combining of peaks and their parameters is based on which sub-range the peaks are in. In particular examples of these embodiments, the sub-ranges are defined based on knowledge of the typical location of spectral peaks, each sub-range encompassing one peak. In other examples, the sub-ranges overlap one another to avoid discrimination against peaks that are near the boundary due to requirements of the peak selection cuts.

In some embodiments of the method, the time segment length is a predetermined number of minutes chosen to optimize over the competing needs of the overall sin, peak resolution, and ability to capture brief events. In other embodiments, the time segment length is a fixed value, but the start times are staggered by an offset in successive analysis runs to improve the detection of shorter peaks by better synchronization of the time segment with their duration in at least one of the runs. For example, using a segment n minutes long, the analysis would be run a times, starting at t=0 min, t=1 min, min, etc.

Further in regard to time segment lengths, in some embodiments the multiple analysis runs are performed first with one segment length and with sequential offset values, then the same sequence is repeated with the next segment length in a series such as 1, 2, 4, 8 . . . minutes, in order to optimally detect all existing peaks and their start and end times. In some embodiments, the time segments used for analysis are not fixed but are rather selected to fit the start and end time of peaks based on pre-analysis peak detection using several different fixed time segment lengths, or a sliding fixed length, or using any other technique. Further, from this type of analysis, the intensity and duration of the motor activity can be discerned, which information is of primary interest to the caregiver in assessing recovery from a patient's ileus state.

In some embodiments, detected peaks can be assigned to one of the digestive organs based via frequency. Such frequency classifications may be based on information published in the literature from experiments with internally placed electrodes. However, the experiments are limited in scope and there is ambiguity and overlap in the spectral regions associated with each major organ. Alternatively, the frequency classifications may be developed based on data acquired from patients using the currently disclosed system. Additionally or alternatively, other parameters beside frequency may be used to help determine whether a peak is from one organ or another. For example, in some embodiments, the width of the peak is measured and used as one such parameter. The peaks from the stomach at about 3 cpm are intrinsically very narrow, on the order of 0.1 cpm hill width at half may (FWHM) and are thus distinguishable from peaks that originate in the colon, which are many times broader. Additionally or alternatively, in some embodiments, another means of discrimination is used to determine which organ is causing a frequency peak. In particular, in some embodiments, the time evolution of the peaks is measured and utilized. The stomach typically responds very quickly to a meal and has a persistent behavior over the subsequent hour or so, with a gradual exponential-like drop off. In contrast, the activity of the colon is episodic and brief, lasting for ten or fifteen minutes without a more symmetric increase and decrease, with the shape of an isolated mountain when viewed in a time-dependent frequency waterfall plot, as visible, for example, in the waterfall plot of FIGS. 9A and 9B. The small intestine pattern is often similar to a mountain range, persisting for many tens of minutes with occasional brief increases.

Another method is used additionally or alternatively in some embodiments to estimate the electrical energy associated with motor activity in a given digestive organ, and by inference, the amount of motor activity, in some such embodiments, the frequency spectrum is divided into regions associated with each organ, for example, the region from 2 to 4 cpm is assigned to the stomach, from 5 to 12 cpm is assigned to the small intestine, and from 12 to 25 cpm is assigned to the colon. However, previous research has indicated that, in certain situations, mixing and segmentation activity of the colon can appear at lower frequencies. As such, in some embodiments, a background signal is subtracted from the frequency spectrum and any peaks identifiable as the stomach and small intestine are also subtracted, so that the remaining signal or frequency spectrum is assigned to the colon. In such embodiments, the frequency of the spectrum region assigned to the colon may be from 1 to 10 cpm, 1 to 15 cpm, to 10 cpm, 5-15 cpm, 10 to 20 cpm, 15 to 25 cpm, or 1 to 25 cpm.

Detecting and quantifying, the peaks, may be made difficult due to the presence of nearby overlapping or weak peaks. Accordingly, in some embodiments, the entire region of the spectrum is summed or integrated across the spectral region for the desired time duration, and the value that results as a function of time serves as a representation of the motor activity of the organ associated with the spectral region.

Additionally or alternatively, in some embodiments, a time series and wavelet analysis may be used to identify a repetitive behavior of a gastrointestinal organ indicative of resumption of motor activity. In some such embodiments, time series data is decomposed into time and frequency space spectrum, and the amplitude of any periodic or repetitive signals is determined and analyzed over time for any variations indicative of a resumption of motor activity.

In addition to the information made evident by the spectral analysis, in some embodiments, motor activity is detected directly in the time series data, in particular, very brief motor activity that persists for only a few cycles, or for a time period considerably shorter than the time segment length used in the spectral analysis is weak in the spectrum and has a low signal to noise ratio, and so it can be easily missed or underestimated. Automated searching through the time series data for specific patterns from a known set of patterns related to motor activity provides an effective means of identifying and quantifying motor activity for brief signals.

Some embodiments employ two or more of the spectral processing approaches described hove. Each of the approaches has its own strengths and, weaknesses. For example, in comparing the peak detection and quantification approach versus the simple integration over a spectral region approach, the peak detection approach intrinsically removes the background that forms a continuum in the spectrum beneath the peaks, improving the signal to noise ratio of the results; accordingly, this approach offers more ability to accurately quantify the level of activity. The integration approach can be improved by first subtracting a general background level that is a function of frequency, and optionally, time. The background can be determined by identifying the amplitude values in areas, where rhythmic peaks from digestive organs are not expected in order to set an overall scale for the background function that should be subtracted. In some embodiments, a region where rhythmic peaks from digestive organs is not expected is determined based on stored information from previous studies of a shape function.

Time series based removal or reduction of artifacts, based on amplitude and pattern, is effective under most circumstances, yet there can be periods of time where the amplitude threshold or other settings used for these procedures should be loosened or tightened. A means of determining this is based on analysis of the section resulting spectrum corresponding to the time period in question. In some embodiments, evaluation of the level of the spectrum beyond the spectral region and in the regions between known peaks provides information that is used to determine whether the artifact reduction in that period was too aggressive or not aggressive enough.

Conductance of the electrical current signal from the organs to and through the skin, resulting in a voltage signal at the electrodes, is a complex process that is affected by a number of variables including the distance from the organ to the skin surface and amount of adipose tissue in between, and the condition of the skin layers and of the skin surface preparation. Comparing the strength of signals between patients, while not the primary focus of the post-operative liens measurement concept, has relevance and will be confounded by these variables. In some embodiments, this is mitigated by calculating a normalization factor based on the strength of the spectrum in frequency regions removed from the primary regions of interest, as described in International PCT Appl. No. PCT/US2015/056282 entitled "Systems and Methods for Processing Electromyographic Signals of the Gastrointestinal Tract" in one non-limiting example, a normalization factor is determined by integration of the spectrum of each channel of data, over the range 25 to 45 cpm, divided by a standard value that is the mean $3f$ a set of such measurements, followed by a square root operation. The range chosen for this example has a generally uneventful spectrum, carrying a certain amount of random noise, but above the signals of interest from the gastrointestinal tract and below those typically seen from the heartbeat. Such normalization of signals removes disparities in motor activity measures between patients and allows for universal measures and thresholds for motor activity to be determined and used to indicate a more absolute value of the activity of the organs. This in turn improves the usefulness of the entire monitoring system.

Yet another type of information that is useful in determining the most accurate measure of motor activity is the behavior of the measured signal during sleep or other restful state. In particular, in some embodiments, the spectrum from such time periods is used to help determine the background spectrum. Any time period during which the rhythmic activity is absent, as seen from a lack of discernible peaks in the spectrum, can be used in such embodiments as a template for modeling the shape of the background curve. The background curve is defined as the spectral power as a function of frequency. In some embodiments, the resulting model is then subtracted from spectra at other times, either directly or with a scaling factor chosen to leave the area between peaks near zero on average.

Another aspect of the present disclosure involves analysis of the measured motor activity as compared to events recorded by the patient or caregiver. Such events may include physical activity, administration of medications, consumption of liquids or solids, gum chewing or other attempts at stimulation of the GI tract. As the external events are recorded, the system of some embodiments monitors the motor activity for changes correlated in time and generates an output of its findings to the staff and/or patient as feedback. In this way, the external activities that are effective in inducing GI motor activity are quickly identified, as are those that do not have a beneficial effect. Such information is valuable in both a research and clinical setting. Similarly, the system monitors and reports whether there was motor activity before or after unscheduled events such as pain episodes or defecation.

In various embodiments, the system of monitoring motor activity is primarily dependent on changes in the amount of rhythmic activity seen in the processed data over time in the patient undergoing the monitoring. In that regard, the absolute value of the readings is not of primary importance since relative measures reveal changes adequately. However, there is significant secondary value in comparing the strength of signals of one patient against various cohorts of previously measured patients. For example, it may be beneficial to assess the strength of a motor activity event compared to that seen in other patients having the same surgery, with a similar body type, of the same gender, and/or of similar age. Developing averages by demographic and surgical type can help healthcare professionals predict how long it will take a patient to recover GI motility. If expected milestones of motor activity strength are not reached within predicted windows of time (e.g., 24 hours, 48 hours, 72 hours, 96 hours, 120 hours, etc), the staff may determine that changes in the patient's treatment protocol are necessary.

The time since surgery to the first signs of activity in each digestive organ is an important parameter, as is the strength of all signals, which tend to be episodic in the sense that they come and go. Tracking of the integrated activity is one measure of recovery, as is the number of individual episodes of activity. Yet another measure that may prove useful is the percent of time that there is activity.

In normal digestive physiology there are well defined motility related events, for example the Giant Migrating Contraction (GMC) in the colon and Migrating Motor Complex (MMC) in the small intestine. The presence of these events would be a strong sign of the return of normal digestive function, hence in some embodiments, the system monitors fir such events, and once detected, the occurrence is reported to the caregiver. The system of some embodiments is configured to identify such patterns from the motor activity and report the same, as an audible or visual alert, through the user interface. In such embodiments, the system identifies and quantifies known gastrointestinal motility patterns in the frequency spectra of each gastrointestinal organ and associates the known gastrointestinal motility patterns with known physiological patterns in each of the gastrointestinal organs. For example, the frequency spectra of each gastrointestinal organ may be evaluated for a strength, duration, and/or number of known gastrointestinal motility patterns. In some embodiments, the system is configured to detect additional or alternative patterns in the electrical signal, such as, for example, the first signals detected in each of the GI organs, the high amplitude propagating contraction (HAPC), and the contractile electrical complex (CEC). Relevant visual results may be provided, for example, in the form of graphs, tables, charts, numbers, images, or words.

Heart rate is affected by eating, increasing briefly but often significantly at the beginning of a meal. The mechanism is not well known but may be connected to the sympathetic and parasympathetic signals in the vagus nerve, which cause opposite effects in the cardiac and digestive systems. That is, the initial phase of eating interrupts ongoing processing in the gut, for example, the interruption of the MMC in the small intestine. In some embodiments, the system is configured to receive a user input indicating the presence or absence of an increase in heart rate at the time of a meal as information that can be used to assess the reaction of the myenteric plexus, which system may be involved in ileus and recovery.

Combined analysis of the motor activity signals in the stomach, small intestine, and colon using any embodiment described above allows calculation of a single metric: the post-operative ileus likelihood predictor (POUT). POILP assesses the chances that the patient will need to stay in the hospital longer than average. The POILP is calculated and updated on a regular basis during the patient monitoring, becoming steadily more reliable as more data is acquired, based on a model driven by analysis of the signals and outcomes of prior patients. Along with the likelihood value, a value for reliability or confidence is also provided. In some embodiments, POILP is calculated based, in part, on the above-described averages developed by demographic and surgical type and the patient's deviation from those averages. In some embodiments, the system contains a database, which stores time averages for a plurality of events, including the detection of the first electrical signals in the stomach, colon, and small intestine, the GMC in the colon, and the MMC in the small intestine. As a patient reaches or fails to reach expected milestones, the system may perform one or more of: revising the patient's PULP, raising the patient's reliability indicator, and narrowing a corresponding confidence interval.

Similarly to the POILP, a hospital readmission likelihood predictor (HRLP) is calculated by some embodiments of the system. The HRLP reflects the probability that if the patient were discharged at a given time they would later have to be readmitted. Calculation of the HRLP is based on a model using data from prior patients and is accompanied by a reliability indicator or confidence interval.

Under some circumstances, the hospital staff may feel that it is safe to discharge a patient who is making good progress, but that continued monitoring is desirable. Such may be the case, for example, if continued progress is being made, but the patient has not yet experienced a bowel movement. Various embodiments of the presently described system can be used for continued monitoring outside of a healthcare facility with little or no changes made. The wireless patches, which are configured to be worn for several days, can remain in place on the patient's abdomen, and the mobile device can either remain with the patient or be replaced by one with the same capability. In some embodiments, during the patient monitoring process, the mobile device used in the healthcare facility may be replaced by the patient's own mobile device such as a smartphone or wearable computing device, in such embodiments, a mobile application is downloaded onto the patient's mobile device. The mobile device of some embodiments continues to upload data to the cloud server wherever the patient is located and the hospital staff will have access to the results through a communicatively coupled computer or any other device or mechanism described above.

Specific patterns seen in the motor activity results may lend themselves to clear guidance on therapeutic interventions. Said patterns, when detected using any of the systems and methods described herein, can be used to inform a patient's treatment protocol. For example, in some embodiments, the system is configured to identify specific patterns within the signals, identify corresponding treatment suggestions stored within a database, and output the appropriate treatment suggestions to caregivers. For example, in some embodiments, treatment suggestions include the administration of medications targeting a particular organ, reduction in use of pain controlling medications such as opioids, feeding of liquids or solids, encouragement of physical activity, and so forth. In other embodiments, healthcare staff are trained to identify the appropriate treatments based on specific patterns flagged by themselves or automatically flagged by the system.

In some embodiments, the system is further configured to provide feedback to the patient in the form of biofeedback to help the patient take advantage of detected motor activity to initiate a bowel movement. It is well known that suppression of urges can lead to constipation and that training to recognize signs of internal activity can assist in overcoming constipation. Alerting patients to measured activity using the patch based system may be an effective biofeedback and training tool, since the patch based system is a very sensitive detector of motor activity and far more sensitive than the patient's own senses.

EXAMPLE

An embodiment of the wireless patch system was applied to a test subject (male, 34 years old, 155 lbs) for over 3 days to demonstrate the feasibility of noninvasively detecting and measuring the presence of key motor activity events. In particular, one wireless patch was placed on the subject's abdomen, and signals were recorded until device battery failure. To apply the patch, the subject's skin was cleaned and prepped with isopropyl alcohol and NuPrep gel (Weaver and Company, Aurora, Colo., USA), then the patch was applied to the upper right corner of the abdomen.

The patch was formed of a flexible substrate material approximately 2.5 inches in diameter on which four Ag/AgCl electrode pairs, a ground Ag/AgCl electrode, a medical grade adhesive, and electronics were printed. A 3V watch battery was also included within the patch to power the electronics. Signals were acquired by the electrodes and amplified and digitized by the electronics. The digitized signals were then transmitted via a Bluetooth® Low Energy (BLE) beacon to a paired iPhone. The iPhone included a specialized iPhone application downloaded and stored in memory, which contained instructions enabling the iPhone to receive, process, and periodically upload the digitized signals to a cloud server. Post-processing was performed on an internet-connected notebook computer using data retrieved from the cloud server and a custom LabVIEW program. Post-processing included methods described elsewhere herein including removal of large amplitude artifacts, band-pass filtering, and Fourier transformation to frequency space over selected time subintervals. Additionally, the subject entered meals, bowel movements, exercise, sleep, and other activities into the iPhone application using the iPhone user interface. The iPhone was configured to transmit these inputs to the cloud server, and a connected computer correlated these activities to the data plots.

Results:

Peaks in the spectrum indicative of rhythmic activity were seen at frequencies across the available spectral range throughout the test period. On a majority of occasions when peaks occurred within the 18-35 cpm range associated with colonic activity, an association with events such as meals or bowel movements was observed. FIGS. 8A and 8B show views of the waterfall plot of the frequency spectrum between 0 and 40 cpm and between 14 and 35 cpm, respectively, computed every 4 minutes and staggered as a function of time for the first 24 hours. The observed peaks appear to depict the contractile electrical complexes. FIG. 7 shows the time dependence of the activity in the 18 to 35 cpm range, computed by summing the spectral amplitude over that range for each 4-minute segment. Meals, bowel movements, and other activities are noted. At the end of 73 hours, the coin cell battery had been depleted, the patch stopped acquiring signals and transmitting data, and the test concluded.

All publications and patent applications mentioned throughout this specification are herein incorporated by reference in their entirety, as if each individual publication or patent application was specifically and individually indicated to be incorporated by reference in its entirety.

As used in the description, and claims, the singular form "a", "an" and "the" include both singular and plural references unless the context clearly dictates otherwise. For example, the term "an electrode pair" may include, and is contemplated to include, a plurality of electrode pairs. At times, the claims and disclosure may include terms such as "a plurality," "one or more," or "at least one," however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending, to voluntarily limit the scope of this application to any single invention or inventive concept, if more than one is disclosed.

Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of detecting, with a surface electrode patch, resumption in motility within a stomach, a small intestine, and a colon of a patient following a surgical procedure, the method comprising:

placing a surface electrode patch onto an abdominal region of a patient, wherein the surface electrode patch comprises a plurality of electrodes arranged in a geometric scheme, and wherein the surface electrode patch is positioned on the patient following a surgical procedure;

acquiring, by the surface electrode patch, an acquired signal comprising a myoelectrical activity signal, wherein said geometric scheme comprises at least two pairs of bipolar electrodes, and at least one pair of bipolar electrodes is parallel to or aligned with at least one other pair of bipolar electrodes;

digitizing the acquired signal with an analog-to-digital converter present on the surface electrode patch;

wirelessly transmitting the digitized signal to a computing device;

automatically applying a time-stamp to the digitized signal;

automatically distinguishing an activity level of each gastrointestinal organ from the time-stamped signal acquired from a patient following a surgical procedure, wherein the activity level of each gastrointestinal organ is distinguished by:
  dividing a frequency spectrum of the time-stamped signal into a plurality of organ-specific spectral regions, wherein a first region corresponds to the stomach, a second region corresponds to the small intestine, and a third region corresponds to the colon,
  integrating the frequency spectrum of the time-stamped signal across each of the plurality of organ-specific spectral regions for a desired time duration, wherein a resultant value as a function of time serves as a representation of a cumulative motor activity of the gastrointestinal organ associated with the organ-specific spectral region, and
  applying a normalization factor to each of the plurality of organ-specific spectral regions, wherein the normalization factor is determined, at least in part, by integration of the frequency spectrum over the range of 25 to 45 cpm, and wherein the normalization factor removes disparities in motor activity measurements between patients based on a strength of the acquired signal due to coupling at a skin surface of the patient and conduction through a body of the patient as a result of one or more of: an amount of adipose tissue, a condition of skin layers, and a condition of a skin surface;

monitoring the cumulative motor activity level of a region of the gastrointestinal organ to identify a change in activity level indicative of a resumption of motor activity in each of the gastrointestinal organs; and comparing the cumulative motor activity level for the patient with the cumulative motor activity level acquired from a previous patient that underwent the same surgical procedure to calculate a post-operative ileus likelihood predictor (POILP), wherein the POILP assesses chances that the patient will develop post-operative ileus, and wherein the POILP is calculated based on a model comparing the time-stamped signal to prior patient signals.

2. The method of claim 1, wherein the first region is 2 to 4 cycles per minute, the second region is 5 to 12 cycles per minute, and the third region is 12 to 40 cycles per minute.

3. The method of claim 1, wherein the surface electrode patch is placed on the patient and positioned so as to avoid a surgical incision or wound.

4. The method of claim 1, wherein monitoring the activity level of each gastrointestinal organ begins in a clinical setting and continues following patient discharge.

5. A method of diagnosing post-operative ileus, the method comprising:
the method of claim 1, wherein the patient is diagnosed with post-operative ileus if one or more of the gastrointestinal organs do not experience a change in activity level indicative of a resumption of motor activity within an expected timeframe.

6. The method of claim 5, wherein the expected timeframe is within 120 hours following placement of the surface electrode patch, wherein the surface electrode patch is placed within 12 hours of a surgical procedure.

7. The method of claim 1, further comprising:
performing one or more of: revising the POILP, raising a POILP reliability indicator, and narrowing a corresponding confidence interval as a patient reaches or fails to reach one or more expected milestones.

8. The method of claim 1, further comprising:
comparing the time-stamped signal to prior patient signals acquired from past patients sharing similar demographic traits as the patient, the demographic traits comprising one or more of: age, weight, gender, race, overall health status, and type of surgery.

9. The method of claim 1, further comprising:
receiving a patient input regarding one or more of: a time of a meal, a time of an activity, a time of taking a medication, a time of a bowel movement, a time of nausea, a time of vomiting, and a time of pain; and
correlating the patient input with the change in activity level of each gastrointestinal organ.

10. The method of claim 1, further comprising:
calculating a background based on values well removed from a series of peaks in the frequency spectra, wherein the series of peaks either reside within or outside a spectral region of interest or are identified based on a general shape of the background; and
subtracting the background from the frequency spectra to produce a net spectral activity value.

11. The method of claim 1, further comprising:
identifying a pattern indicative of a blockage in one or more gastrointestinal organs.

12. The method of claim 1, wherein the frequency spectra during periods of sleep are used as a background or baseline to evaluate the frequency spectra during wakefulness.

13. The method of claim 1, further comprising:
representing the activity level of each gastrointestinal organ as a percentage of a time there was motor activity above a given threshold for each gastrointestinal organ.

14. The method of claim 1, further comprising:
identifying and quantifying known gastrointestinal motility patterns in the frequency spectra of each gastrointestinal organ; and
associating the known gastrointestinal motility patterns with known physiological patterns in each of the GI organs.

15. The method of claim 1, further comprising:
predicting a likelihood of a bowel movement, flatus, nausea, and vomiting occurring in a specified time period based on the activity level of each of the recorded gastrointestinal organs.

16. The method of claim 1, further comprising:
administering a therapy to the patient; and
monitoring the activity level of each gastrointestinal organ to determine whether change in activity level occurs during or after administration of the therapy.

17. The method of claim 1, further comprising:
alerting the patient to an increase in activity level of one or more of the gastrointestinal organs to encourage the patient to attempt a bowel movement.

18. The method of claim 1, wherein the geometric scheme comprises at least four pairs of bipolar electrodes, and wherein each pair of bipolar electrodes is perpendicular to at least one other pair of bipolar electrodes.

19. The method of claim 1, wherein the two pairs of bipolar electrodes are aligned radially.

20. The method of claim 1, further comprising:
calculating a hospital readmission likelihood predictor (HRLP), wherein the HRLP assesses chances that the patient will need to stay in a hospital longer than average, and wherein the HRLP is calculated based on a model comparing the time-stamped signal to prior patient signals, the prior patient signals associated with known prior patient outcomes.

21. A method of detecting, with a surface electrode patch, resumption in motility within a stomach, a small intestine, and a colon of a patient following a surgical procedure, the method comprising:
placing a surface electrode patch onto an abdominal region of a patient, wherein the surface electrode patch comprises a plurality of electrodes arranged in a geometric scheme, and wherein the surface electrode patch is positioned on the patient following a surgical procedure;
acquiring, by the surface electrode patch, an acquired signal comprising a myoelectrical activity signal, wherein said geometric scheme comprises at least two pairs of bipolar electrodes, and at least one pair of bipolar electrodes is parallel to or aligned with at least one other pair of bipolar electrodes;
digitizing the acquired signal with an analog-to-digital converter present on the surface electrode patch;
wirelessly transmitting the digitized signal to a computing device;
automatically applying a time-stamp to the digitized signal;
automatically distinguishing an activity level of each gastrointestinal organ from the time-stamped signal acquired from a patient following a surgical procedure, wherein the activity level of each gastrointestinal organ is distinguished by:
identifying a first threshold based on a background or baseline amplitude,
identifying a second threshold that is higher than the first threshold, the second threshold being based on a percentile rank of all set points in the time-stamped signal,
locating one or more peaks that are above an amplitude of the second threshold to yield one or more identified peaks, applying a set of cuts to the one or more identified peaks, calculating a volume of the one or more identified peaks above the first threshold, dividing the one or more identified peaks into one or more subsets based on a plurality of organ-specific spectral regions, wherein a first region corresponds to the stomach, a second region corresponds to the small intestine, and a third region corresponds to the colon, and integrating the one or more subsets across each of the plurality of organ-specific spectral regions for a desired time duration, wherein a resultant value as a function of time serves as a representation of a cumulative motor activity of the gastrointestinal organ associated with the organ-specific spectral region, monitoring the cumulative motor activity level of a region of the gastrointestinal organ to identify a change in activity level indicative of a resumption of motor activity in each of the gastrointestinal organs; and comparing the cumulative motor activity level for the patient with the cumulative motor activity level acquired from a previous patient that underwent the same surgical procedure to calculate a post-operative ileus likelihood predictor (POILP), wherein the POILP assesses chances that the patient will develop post-operative ileus, and wherein the POILP is calculated based on a model comparing the time-stamped signal to prior patient signals.

* * * * *